(12) United States Patent
Rapoport et al.

(10) Patent No.: US 9,482,643 B2
(45) Date of Patent: Nov. 1, 2016

(54) MEANS AND METHODS USING PARAMAGNETIC AGENTS FOR IN VITRO DIAGNOSTIC APPLICATIONS

(71) Applicant: Aspect Imaging Ltd., Shoham (IL)

(72) Inventors: Uri Rapoport, Moshav Ben Shemen (IL); Camila Cavallotti, Novara (IT); Simonetta Geninatti Crich, Turin (IT)

(73) Assignee: Aspect Imaging Ltd., Shoham (IL)

( * ) Notice: Subject to any disclaimer, the term of this patent is extended or adjusted under 35 U.S.C. 154(b) by 81 days.

(21) Appl. No.: 14/090,298

(22) Filed: Nov. 26, 2013

(65) Prior Publication Data

US 2015/0147746 A1    May 28, 2015

(51) Int. Cl.
    *G01R 33/12*    (2006.01)
    *G01N 27/74*    (2006.01)
    *A61B 5/05*    (2006.01)

(52) U.S. Cl.
    CPC ......... *G01N 27/745* (2013.01); *G01R 33/1269* (2013.01); *G01R 33/1276* (2013.01); *A61B 5/05* (2013.01)

(58) Field of Classification Search
    None
    See application file for complete search history.

(56) References Cited

U.S. PATENT DOCUMENTS

| 2008/0246476 A1* | 10/2008 | Rapoport | G01R 33/383 324/307 |
| 2011/0012596 A1* | 1/2011 | Menon | G01N 24/08 324/309 |
| 2011/0091987 A1 | 4/2011 | Weissleder et al. | |
| 2012/0223705 A1* | 9/2012 | Lowery | A61B 5/055 324/307 |

OTHER PUBLICATIONS

Shag et al., "Magnetic Nanoparticles and microNMR for Diagnostic Applications", Theranostics, 2012, pp. 55-65, vol. 2(1).

* cited by examiner

*Primary Examiner* — Rebecca Martinez
(74) *Attorney, Agent, or Firm* — Pearl Cohen Zedek Latzer Baratz LLP

(57) ABSTRACT

A method of detecting a target biochemical molecular species or at least one property correlated with the occurrence of the biochemical molecular species in a sample whose main component is water. The method includes: obtaining a sample whose main component is water; providing Functionalized Paramagnetic Particles (FPP) including a paramagnetic core and a moiety configured to interact with the target biochemical molecular species or with molecules collectively reporting on a property of the target biochemical molecular species; contacting the FPP with the sample; exposing the sample to an applied magnetic field; measuring a change in a nuclear relaxation property of the sample; and correlating the change to the presence of the biochemical molecular species in the sample or to at least one property correlated with the occurrence of the biochemical molecular species in the sample.

17 Claims, 9 Drawing Sheets

MEANS AND METHODS USING PARAMAGNETIC AGENTS FOR IN VITRO DIAGNOSTIC APPLICATIONS

FIELD OF THE INVENTION

The present invention relates to the field of magnetic resonance-based systems and related methods, for diagnostic in vitro applications, and more particularly, to systems that use magnetic resonance $^1$H-relaxometry for detection of a biomarker of interest and methods thereof.

BACKGROUND OF THE INVENTION

Biomarkers are objective measures or indicators which are used to evaluate disease versus normal biological processes or responses to a drug or treatment. Many different biomarker types are utilized for various purposes in the pharmaceutical process. Biomarker types and applications thereof are broadly used in the clinical and healthcare spectrum, for example biomarkers for risk assessment, permit the estimation of the risk of an individual to develop a particular disease. Other types of biomarkers include: biomarkers for earlier and more specific indication of a compound's toxicity; biomarkers for prognosis (providing information about the expected course of a disease); biomarkers for patient stratification (allowing to identify the best treatment for a disease); and, biomarkers for therapy monitoring (providing information at an early stage as to whether treatment is working or if the disease is getting worse).

Biosensing strategies using magnetic nanoparticles have been reported in the relevant art. These publications describe magnetic resonance-related techniques based on $T_2$-relaxation time measurements. For example, US application No. 2011/0091987A1 and a recently published scientific article (Huilin Shao et al., Theranostics 2012) describe NMR-based detection mechanism for diagnostic applications. In order to increase the sensitivity of the detection, magnetic nanoparticles have been used that are specifically designed and shown to improve T2* changes. These particles consist of ferrite particles or crossed linked iron oxide.

Thus, there is still a long felt need to provide sensitive and reliable means and methods for the identification and quantification of a biomarker of interest for diagnostic applications.

SUMMARY OF THE INVENTION

It is an object of the present invention to disclose a method for detecting a target biochemical molecular species or at least one property correlated with the occurrence of said biochemical molecular species in a sample whose main component is water, comprising;
a. obtaining a sample whose main component is water;
a. providing Functionalized Paramagnetic Particles (FPP) comprising a paramagnetic core and a moiety configured to interact with said target biochemical molecular species or with molecules collectively reporting on a property of said target biochemical molecular species;
a. contacting said FPP with said sample;
a. exposing said sample to an applied magnetic field; and,
a. measuring a change in a nuclear relaxation property of said sample, caused by said interaction between said FPP and said biochemical molecular species or said molecules collectively reporting on a property of said target biochemical molecular species; in the applied magnetic field; and,
a. correlating said change to the presence of said biochemical molecular species in said sample or to at least one property correlated with the occurrence of said biochemical molecular species in said sample;
wherein a change in T.sub.1 nuclear relaxation property of the water protons in said sample is correlated to the presence of said target biochemical molecular species or to at least one property correlated with the occurrence of said biochemical molecular species in said sample, further wherein said FPP comprises a non ferrous oxide paramagnetic core.

It is another object of the present invention to disclose the method as defined above, comprising an additional step of performing two or more measurements to determine the relaxation time of the sample, wherein the measurements are performed before and after at least one addition of said FPP.

It is another object of the present invention to disclose the method as defined above, comprising an additional step of detecting said target biochemical molecular species and/or characterizing at least one property correlated with the occurrence of said biochemical molecular species in vitro.

It is another object of the present invention to disclose the method as defined above, comprising an additional step of forming said FPP as a single molecule, a multimeric system, a micro-sized vesicle or particle, a nano-sized vesicle or particle, a liposome, a probe or any combination thereof.

It is another object of the present invention to disclose the method as defined above, comprising an additional step of selecting said sample from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

It is another object of the present invention to disclose the method as defined above, comprising an additional step of selecting said sample from a group comprising a biological fluid, a biological tissue, a tissue extract, an industrial fluid, food sample, a beverage, wine, water, potable water, sewage, irrigation water, sea water, river water, lake water, industrial effluent, farm effluent, effluent from human habitation, road runoff, cleaning fluid, a gas sample or any combination thereof.

It is another object of the present invention to disclose the method as defined above, comprising an additional step of selecting said biological fluid from a group comprising urine, blood, lymph, plasma, cerebrospinal fluid, saliva, amniotic fluid, bile and tears.

It is another object of the present invention to disclose the method as defined above, comprising an additional step of providing said sample within a production process.

It is another object of the present invention to disclose the method as defined above, comprising an additional step of selecting said production process in an industrial area, said industrial area is a member of a group consisting of the pharmaceuticals, food production, beverage production, chemical refining, chemical processing, medical products, biological products, metal casting, metal refining, desalination, fluid purification, and sewage processing.

It is another object of the present invention to disclose the method as defined above, comprising an additional step of analyzing at least one characteristic or property of said target molecular species, said characteristic or property is selected from a group comprising concentration, permeability, oxidation state, redox characteristic (reduction-oxidation state), activation state and any combination thereof.

It is another object of the present invention to disclose the method as defined above, comprising an additional step of applying a magnetic field, thereby enhancing the change in a paramagnetic nuclear relaxation property of said sample upon comparing relaxation rates at two different magnetic fields.

It is another object of the present invention to disclose the method as defined above, comprising an additional step of measuring a change in a nuclear relaxation property of said sample using a portable NMR or MRI measuring means.

It is another object of the present invention to disclose the method as defined above, comprising an additional step of measuring a change in a nuclear relaxation property of said sample using a magnetic resonance device (MRD) consisting of magnets housed within a cage.

It is another object of the present invention to disclose the method as defined above, comprising an additional step of measuring a change in a nuclear relaxation property of said sample using a self-fastening cage type of a magnetic resonance device (MRD).

It is another object of the present invention to disclose the method as defined above, In a self-fastening cage of a magnetic resonance device (MRD) (300), a method according to claim 1 comprising an additional step of providing a homogeneous, stable and uniform magnetic field therein, further wherein said self-fastening cage type MRD additionally characterized by an outside shell comprising at least three flexi-jointed superimposed walls (1).

It is another object of the present invention to disclose in a self-fastening cage type MRD (300), a method as defined above comprising an additional step of providing an MRD characterized by an outside shell; said outside shell comprising at least three flexi-jointed superimposed walls (1) disposed in a predetermined clockwise or counterclockwise arrangement; said MRD comprising:
a. at least six side-magnets (2) arranged in two equal groups being in a face-to-face orientation in a magnetic connection with said outside shell, increasing the overall strength of the magnetic field provided in said cage;
b. at least two pole-magnet pieces (3), arranged in a face-to-face orientation in between said side-magnets (2);
c. at least two main-magnets (4), located on said pole-pieces (3), arranged in a face-to-face orientation, generating the static magnetic field therein said cage; and,
d. shimming mechanism, said mechanism is selected from a group consisting of an array of active shim coils, passive shimming elements or a combination thereof;
wherein at least a portion of said side-magnets (2) are superconductors or ferromagnets.

It is another object of the present invention to disclose the method as defined above, comprising an additional step of providing a magnetic resonance device adapted to producing high contrast high resolution images of said sample.

It is another object of the present invention to disclose the method as defined above, comprising an additional step of providing a magnetic resonance device comprising:
a. an envelope for least partially confining said sample;
b. a plurality of magnets located at least partially around said envelope, said plurality of magnets comprising:
 i. a least one first magnet configured to provide a high magnetic field for generating multiple time-resolved one or more first images at high resolution of at least a portion of said sample; and
 ii. a least one second magnet configured to provide a low magnetic field for generating multiple time-resolved one or more second images at high contrast of at least portion of same said sample; wherein at least one image of said first images and at least one image of said second images being generated in a time no greater than approximately the time between two first images; and,
c. a CPU to process said images comprising a computer readable medium containing instructions for generating at least one third image superimposing at least one image of said first images with at least one image of said second images.

It is another object of the present invention to disclose the method as defined above, comprising additional steps of
a. generating multiple time resolved one or more first images at high resolution of at least a portion of said sample;
b. generating multiple time resolved one or more second images at high contrast of at least portion of same said sample; and
c. superimposing at least one image of said first images with at least one image of said second images;
whereby a high-contrast, high resolution real-time continuous image of said sample is obtained.

It is another object of the present invention to disclose the method as defined above, comprising an additional step of selecting said at least one first magnet to be of 2 Tesla and lower.

It is another object of the present invention to disclose the method as defined above, comprising an additional step of selecting said at least one first magnet to be of 2 Tesla and higher.

It is another object of the present invention to disclose the method as defined above, comprising an additional step of selecting said at least one first magnet from a group consisting of permanent magnets, electromagnets, superconducting magnets, and any combination thereof.

It is another object of the present invention to disclose the method as defined above, comprising an additional step of selecting said at least one second magnet to be of 2 Tesla and lower.

It is another object of the present invention to disclose the method as defined above, comprising an additional step of selecting said at least one second magnet to be of 2 Tesla and higher.

It is another object of the present invention to disclose the method as defined above, comprising an additional step of selecting said at least one second magnet from a group consisting of permanent magnets, electromagnets, superconducting magnets, and any combination thereof.

It is another object of the present invention to disclose the method as defined above, comprising an additional step of generating a magnetic resonance signal in the range of about 0.1 Tesla and about 10 Tesla.

It is another object of the present invention to disclose the method as defined above, comprising an additional step of generating a magnetic resonance signal in the range of 2 Tesla and lower.

It is another object of the present invention to disclose the method as defined above, comprising an additional step of generating a magnetic resonance signal in the range of 2 Tesla and higher.

It is another object of the present invention to disclose the method as defined above, further comprises steps of applying a magnetic resonance frequency in the range of about 5 MHz to about 40 MHz.

It is another object of the present invention to disclose the method as defined above, comprising an additional step of selecting said magnets from a group consisting of permanent magnets, electromagnets, superconducting magnets, and any combination thereof.

It is another object of the present invention to disclose the method as defined above, comprising an additional step of selecting said moiety from a group comprising antibodies, antibody fragments, monoclonal antibody, receptors, ligands, macromolecules, peptides, hormones, fatty acids, lipids, receptor agonists and antagonists, amino acids, sugars, lectins, albumins, polycarbon molecules, glycoproteins, nucleic acids, pegylated molecules, liposomes, chelators, cells, viruses, chemotherapeutic agents and any combination thereof.

It is another object of the present invention to disclose the method as defined above, comprising an additional step of selecting said target biochemical molecular species from a group comprising a biological molecule, a chemical molecule, an analyte, a contaminant, a particle, a pathogen or any combination thereof.

It is another object of the present invention to disclose the method as defined above, comprising an additional step of selecting said target biochemical molecular species from a group comprising a protein, a pathogen, a prion, a virus, a bacteria, a contaminant, a pathological isoform, a biomarker, an allergen, a neurotransmitter, an antigenic determinant, an epitope, a cell marker, cell membrane marker or epitope, a membrane marker, an enzyme, a chemical molecule, an analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue and any combination thereof.

It is another object of the present invention to disclose the method as defined above, comprising an additional step of selecting said analyte from a group comprising an organic analyte and an inorganic analyte.

It is another object of the present invention to disclose the method as defined above, comprising an additional step of selecting said inorganic analyte from a group comprising molecular oxygen, oxygen-containing radicals and combinations thereof.

It is another object of the present invention to disclose the method as defined above, comprising an additional step of detecting oxygen-containing radicals "ad hoc" generated, for assessing the anti-oxidant properties of the sample.

It is another object of the present invention to disclose the method as defined above, comprising an additional step of selecting said paramagnetic core as a metal ion, a metal complex, oxides of a metal ion, oxides of a transition metal, mixed oxides of a transition metal and their mixtures.

It is another object of the present invention to disclose the method as defined above, comprising an additional step of selecting said paramagnetic core from a group comprising metal complexes, aggregates of metal complexes, polymer-bound metal complexes, stable organic radicals and any combination thereof.

It is another object of the present invention to disclose the method as defined above, comprising an additional step of selecting said metal ion from a group comprising an ion of nickel, iron, manganese, copper, gadolinium, europium and mixtures thereof.

It is another object of the present invention to disclose the method as defined above, based on a competition assay for assessing redox characteristics, comprising steps of detecting differences in Paramagnetic Relaxation Enhancement (PRE) properties induced by a change in at least one redox characteristic of said FPP, using an applied magnetic field.

It is another object of the present invention to disclose the method as defined above, comprising an additional step of selecting said redox characteristic from a group comprising lipid peroxidation, lipid peroxidation followed by a change in membrane permeability, redox potential of metal ions, formation and cleavage of disulfide bonds, oxidation state, antioxidant activity and any combination thereof.

It is another object of the present invention to disclose the method as defined above, comprising an additional step of providing said FPP as a liposome loaded with a plurality of paramagnetic payloads.

It is another object of the present invention to disclose the method as defined above, comprising an additional step of applying a magnetic field, thereby enhancing a change in the permeability of said liposome so as to affect a nuclear relaxation property of said sample.

It is another object of the present invention to disclose the method as defined above, further comprising steps of applying a magnetic field, thereby enhancing a change in at least one of cleavage or formation of disulfide bonds of said moiety so as to affect a nuclear relaxation property of said sample.

It is another object of the present invention to disclose the method as defined above, further comprising steps of applying a magnetic field, thereby affecting at least one property of said FPP selected from a group comprising concentration, lipid peroxidation, membrane permeability, redox potential, formation and cleavage of disulfide bonds, oxidation state, redox potential, activation state, binding affinity, and any combination thereof, so as to induce a change in a nuclear relaxation property of said sample.

It is another object of the present invention to disclose the method as defined above, comprising an additional step of conjugating said liposome with a site-specific ligand.

It is another object of the present invention to disclose the method as defined above, comprising an additional step of conjugating said liposome with a biotin activated molecule.

It is another object of the present invention to disclose the method as defined above, comprising an additional step of providing said FPP as a biotinylated liposome.

It is an object of the present invention to disclose a method for detection of a biomarker in a sample whose main component is water, comprising steps of:

a. obtaining a sample whose main component is water;
b. providing liposomes loaded with a plurality of paramagnetic agents, said liposomes are conjugated with a site specific moiety configured to interact with said biomarker in said sample;
c. contacting said liposomes with said sample under conditions that allow the interaction between the site specific moiety and said biomarker;
d. exposing said sample to an applied magnetic field; and,
e. measuring a change in a nuclear relaxation property of said sample caused by said interaction between the liposomes and said biomarker in the applied magnetic field;

wherein a change in $T_1$ nuclear relaxation property is correlated to the presence of said biomarker in said sample.

It is another object of the present invention to disclose the method as defined above, comprising additional steps of:

a. providing biotinylated liposomes; said liposomes loaded with a plurality of paramagnetic agents;
b. providing biotinylayed ligands, said ligands configured to interact with said biomarker;
c. providing activated avidin molecules;
d. contacting said biotinylated liposomes, said biotinylayed ligands and said activated avidin molecules with said sample so as to enable avidin-biotin interaction, thereby forming complexes comprising said liposomes, said ligand and said biomarker; such that said complexes are specific to said biomarker; and, e. measuring a change in a nuclear relaxation property of said sample caused by said complex formation in the applied magnetic field;

wherein a change in T.sub.1 nuclear relaxation property is correlated to the presence of said biomarker in said sample.

It is an object of the present invention to disclose a system for detecting a target biochemical molecular species or at least one property correlated with the occurrence of said biochemical molecular species in a sample whose main component is water, comprising;

a. a magnetic resonance device (MRD) configured to measure a change in nuclear relaxation property of said sample; and, b. a plurality of Functionalized Paramagnetic Particles (FPP) said FPP comprising a paramagnetic core and a moiety configured to interact with said target biochemical molecular species or with molecules collectively reporting on a property of said target biochemical molecular species;

wherein a change in T.sub.1 nuclear relaxation property of water protons in said sample measured by said MRD is correlated to the presence of said target biochemical molecular species and/or to the at least one property correlated with the occurrence of said biochemical molecular species in said sample, further wherein said FPP comprises a non ferrous oxide paramagnetic core.

It is another object of the present invention to disclose the system as defined above, further comprises means for detecting said target biochemical molecular species and/or characterizing at least one property correlated with the occurrence of said biochemical molecular species in vitro.

It is another object of the present invention to disclose the system as defined above, wherein said FPP is formed as a single molecule, a multimeric system, a micro-sized vesicle or particle, a nano-sized vesicle or particle, a liposome, a probe and any combination thereof.

It is another object of the present invention to disclose the system as defined above, wherein said sample is selected from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

It is another object of the present invention to disclose the system as defined above, wherein said sample is further selected from a group comprising a biological fluid, a biological tissue, a tissue extract, an industrial fluid, food sample, a beverage, wine, water, potable water, sewage, irrigation water, sea water, river water, lake water, industrial effluent, farm effluent, effluent from human habitation, road runoff, cleaning fluid, a gas sample or any combination thereof.

It is another object of the present invention to disclose the system as defined above, wherein said biological fluid is selected from a group comprising urine, blood, lymph, plasma, cerebrospinal fluid, saliva, amniotic fluid, bile and tears.

It is another object of the present invention to disclose the system as defined above, wherein said sample is provided within a production process.

It is another object of the present invention to disclose the system as defined above, wherein said production process is in an industrial area, said industrial area is a member of a group consisting of the pharmaceuticals, food production, beverage production, chemical refining, chemical processing, medical products, biological products, metal casting, metal refining, desalination, fluid purification, and sewage processing.

It is another object of the present invention to disclose the system as defined above, wherein said property is selected from a group comprising concentration, permeability, oxidation state, redox characteristic (reduction-oxidation state), activation state and any combination thereof.

It is another object of the present invention to disclose the system as defined above, wherein said magnetic resonance device (MRD) is configured to enhance the change in a paramagnetic nuclear relaxation property of said sample upon comparing relaxation rates at two different magnetic fields.

It is another object of the present invention to disclose the system as defined above, wherein said magnetic resonance device (MRD) is a portable NMR or MRI measuring means.

It is another object of the present invention to disclose the system as defined above, wherein said magnetic resonance device (MRD) consists of magnets housed within a cage.

It is another object of the present invention to disclose the system as defined above, wherein said magnetic resonance device (MRD) is a self-fastening cage type of a magnetic resonance device (300).

It is another object of the present invention to disclose in a self-fastening cage of a magnetic resonance device (MRD) (300), a system as defined above wherein said self-fastening cage type MRD additionally characterized by an outside shell comprising at least three flexi-jointed superimposed walls (1).

It is another object of the present invention to disclose in a self-fastening cage type MRD (300), a system as defined above further comprises a MRD characterized by an outside shell; said outside shell comprising at least three flexi-jointed superimposed walls (1) disposed in a predetermined clockwise or counterclockwise arrangement; said MRD comprising:

a. at least six side-magnets (2) arranged in two equal groups being in a face-to-face orientation in a magnetic connection with said outside shell, increasing the overall strength of the magnetic field provided in said cage;

b. at least two pole-magnet pieces (3), arranged in a face-to-face orientation in between said side-magnets (2);

c. at least two main-magnets (4), located on said pole-pieces (3), arranged in a face-to-face orientation, generating the static magnetic field therein said cage; and, d. shimming mechanism, said mechanism is selected from a group consisting of an array of active shim coils, passive shimming elements or a combination thereof;

wherein at least a portion of said side-magnets (2) are superconductors or ferromagnets.

It is another object of the present invention to disclose the system as defined above, wherein said MRD is configured to produce high contrast high resolution images of said sample.

It is another object of the present invention to disclose the system as defined above, wherein said magnetic resonance device comprising:

a. an envelope for least partially confining said sample;

b. a plurality of magnets located at least partially around said envelope, said plurality of magnets comprising:
  i. a least one first magnet configured to provide a high magnetic field for generating multiple time-resolved one or more first images at high resolution of at least a portion of said sample; and
  ii. a least one second magnet configured to provide a low magnetic field for generating multiple time-resolved one or more second images at high contrast of at least portion of same said sample; wherein at least one image of said first images and at least one image of said second images being generated in a time no greater than approximately the time between two first images; and, c. a CPU to process said images comprising a computer readable medium containing instructions for generating at least one third image superimposing at least one image of said first images with at least one image of said second images, whereby a high contrast, high resolution real time continues image of said sample is obtained.

It is another object of the present invention to disclose the system as defined above, wherein said at least one first magnet is of 2 Tesla and lower.

It is another object of the present invention to disclose the system as defined above, wherein said at least one first magnet is of 2 Tesla and higher.

It is another object of the present invention to disclose the system as defined above, wherein said at least one first magnet is selected from a group consisting of permanent magnets, electromagnets, superconducting magnets, and any combination thereof.

It is another object of the present invention to disclose the system as defined above, wherein said at least one second magnet is of 2 Tesla and lower.

It is another object of the present invention to disclose the system as defined above, wherein said at least one second magnet is of 2 Tesla and higher.

It is another object of the present invention to disclose the system as defined above, wherein said at least one second magnet is selected from a group consisting of permanent magnets, electromagnets, superconducting magnets, and any combination thereof.

It is another object of the present invention to disclose the system as defined above, wherein said magnetic resonance device (MRD) is configured to generate a magnetic resonance signal in the range of about 0.1 Tesla and about 10 Tesla.

It is another object of the present invention to disclose the system as defined above, wherein said magnetic resonance device (MRD) is configured to generate a magnetic resonance signal in the range of 2 Tesla and lower.

It is another object of the present invention to disclose the system as defined above, wherein said magnetic resonance device (MRD) is configured to generate a magnetic resonance signal in the range of 2 Tesla and higher.

It is another object of the present invention to disclose the system as defined above, wherein said magnetic resonance device (MRD) is configured to generate a magnetic resonance frequency in the range of about 5 MHz to about 40 MHz.

It is another object of the present invention to disclose the system as defined above, wherein said magnets are selected from a group consisting of permanent magnets, electromagnets, superconducting magnets, and any combination thereof.

It is another object of the present invention to disclose the system as defined above, wherein said moiety is selected from a group comprising antibodies, antibody fragments, monoclonal antibody, receptors, ligands, macromolecules, peptides, hormones, fatty acids, lipids, receptor agonists and antagonists, amino acids, sugars, lectins, albumins, polycarbon molecules, glycoproteins, nucleic acids, pegylated molecules, liposomes, chelators, cells, viruses, chemotherapeutic agents and any combination thereof.

It is another object of the present invention to disclose the system as defined above, wherein said target biochemical molecular species is selected from a group comprising a biological molecule, a chemical molecule, an analyte, a contaminant, a particle, a pathogen or any combination thereof.

It is another object of the present invention to disclose the system as defined above, wherein said target biochemical molecular species is selected from a group comprising a protein, a pathogen, a prion, a virus, a bacteria, a contaminant, a pathological isoform, a biomarker, an allergen, a neurotransmitter, an antigenic determinant, an epitope, a cell marker, cell membrane marker or epitope, a membrane marker, an enzyme, a chemical molecule, an analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue and any combination thereof.

It is another object of the present invention to disclose the system as defined above, wherein said analyte is selected from a group comprising an organic analyte and an inorganic analyte.

It is another object of the present invention to disclose the system as defined above, wherein said inorganic analyte is selected from a group comprising molecular oxygen, oxygen-containing radicals and combinations thereof.

It is another object of the present invention to disclose the system as defined above, wherein said oxygen-containing radicals are "ad hoc" generated radicals, for assessing the anti-oxidant properties of the sample.

It is another object of the present invention to disclose the system as defined above, wherein said paramagnetic core is selected from a group comprising a metal ion, a metal complex, oxides of a metal ion, oxides of a transition metal, mixed oxides of a transition metal and their mixtures.

It is another object of the present invention to disclose the system as defined above, wherein said metal ion is selected from a group comprising an ion of nickel, iron, manganese, copper, gadolinium, europium and mixtures thereof.

It is another object of the present invention to disclose the system as defined above, wherein said redox characteristic is selected from a group comprising lipid peroxidation, lipid peroxidation followed by a change in membrane permeability, redox potential of metal ions, formation and cleavage of disulfide bonds, oxidation state, antioxidant activity and any combination thereof.

It is another object of the present invention to disclose the system as defined above, wherein said FPP is a liposome loaded with a plurality of paramagnetic payloads.

It is another object of the present invention to disclose the system as defined above, comprising means for enhancing a change in the permeability of said liposome so as to affect a nuclear relaxation property of said sample.

It is another object of the present invention to disclose the system as defined above, wherein said system is adapted to detect a change in at least one of cleavage or formation of disulfide bonds of said moiety so as to affect a nuclear relaxation property of said sample.

It is another object of the present invention to disclose the system as defined above, wherein said property correlated with the occurrence of said biochemical molecular species is selected from a group comprising concentration, lipid peroxidation, membrane permeability, redox potential, formation and cleavage of disulfide bonds, oxidation state, redox potential, activation state, binding affinity, and any combination thereof.

It is another object of the present invention to disclose the system as defined above, wherein said liposome is conjugated with a site-specific ligand.

It is another object of the present invention to disclose the system as defined above, wherein said liposome is conjugated with a biotin activated molecule.

It is another object of the present invention to disclose the system as defined above, wherein said FPP is a biotinylated liposome.

It is an object of the present invention to disclose a system for detection of a biomarker in a sample, whose main component is water, comprising:
a. a sample whose main component is water;
b. liposomes loaded with a plurality of paramagnetic agents, said liposomes are conjugated with a site specific moiety configured to interact with said biomarker in said sample;
c. a magnetic resonance device (MRD) configured to measure a change in a nuclear relaxation property of a sample whose main component is water removed from said production batch or continuous flow of said FBW or biological fluid;
wherein a change in $T_1$ nuclear relaxation property of the water protons in said sample is correlated to the presence of said biomarker in said sample.

It is an object of the present invention to disclose the use of Functionalized Paramagnetic Particles (FPP) to detect the presence or at least one other characteristic of a target biochemical molecular species within a sample whose main component is water, said FPP comprising a paramagnetic core and a moiety configured to interact with said target biochemical molecular species or with molecules collectively reporting on a property of said target biochemical molecular species; wherein a change in $T_1$ nuclear relaxation property of water protons within said sample measured by a generated applied magnetic field is correlated to the presence or at least one other characteristic of said target biochemical molecular species in said sample.

It is an object of the present invention to disclose the use as defined above further adapted to detect at least one property correlated with the occurrence of said biochemical molecular species in said sample.

It is an object of the present invention to disclose a method of establishing the redox properties of a production batch or continuous flow of a Foodstuff, Beverage or Wine (FBW) or of a biological fluid, comprising the steps of:
a. obtaining a sample removed from said production batch or continuous flow of said FBW or from said biological fluid;
b. providing Functionalized Paramagnetic Particles (FPP) configured to change their redox property upon interaction with dissolved molecular oxygen or "ad hoc" generated radicals of said removed sample;
c. contacting said FPP with said removed sample;
d. exposing said removed sample to an applied magnetic field; and,
e. measuring a change in a nuclear relaxation property of said removed sample caused by said change in the redox properties of said FPP in the applied magnetic field;
wherein a change in $T_1$ nuclear relaxation property is correlated with the presence and/or concentration of said molecular oxygen or of the "ad hoc" generated radicals of said removed sample, thereby establishing the redox properties of said production batch or continuous flow of said FBW or of said biological fluid.

It is another object of the present invention to disclose the method as defined above, comprising an additional step of providing said FPP conjugated with at least one moiety configured to interact with dissolved molecular oxygen or with "ad hoc" generated radicals.

It is another object of the present invention to disclose the method as defined above, comprising an additional step of selecting said moiety from a group comprising a lipid, a fatty acid, an amino acid, a peptide, a protein, a molecule containing at least one disulfide bond, a liposome and any combination thereof.

It is another object of the present invention to disclose the method as defined above, comprising an additional step of measuring a change in a nuclear relaxation property of said sample caused by a change in the antioxidant activity of said removed sample in the applied magnetic field.

It is another object of the present invention to disclose the method as defined above, comprising an additional step of measuring a difference in Paramagnetic Relaxation Enhancement (PRE) property of said removed sample caused by said interaction of said FPP with said dissolved molecular oxygen or with said "ad hoc" generated radicals.

It is another object of the present invention to disclose the method as defined above, comprising an additional step of contacting said removed sample with FPP configured to form a liposome structure, said FPP comprising a paramagnetic core and a fatty acid moiety, wherein peroxidation of said fatty acid moiety substantially changes the permeability of said liposome.

It is an object of the present invention to disclose the method as defined above, comprising an additional step of measuring a change in a nuclear relaxation property of said removed sample based on competition for molecular oxygen consumption.

It is another object of the present invention to disclose the method as defined above, comprising an additional step of providing said FPP comprising a paramagnetic core selected from a group comprising a metal ion, a metal complex, oxides of a metal ion, oxides of a transition metal, mixed oxides of a transition metal and their mixtures.

It is another object of the present invention to disclose the method as defined above, comprising an additional step of selecting said metal ion from a group comprising an ion of nickel, iron, manganese, copper, gadolinium, dysprosium, europium and mixtures thereof.

It is another object of the present invention to disclose the method as defined above, comprising an additional step of selecting said biological fluid from a group comprising urine, blood, lymph, plasma, cerebrospinal fluid, saliva, amniotic fluid, bile and tears.

It is an object of the present invention to disclose a system for establishing the redox properties of a production batch or continuous flow of a Foodstuff, Beverage, Wine (FBW) or of a biological fluid, comprising:
a. a magnetic resonance device (MRD) configured to measure a change in a nuclear relaxation property of a sample removed from said production batch or continuous flow of said FBW or of said biological fluid; and,
b. a plurality of Functionalized Paramagnetic Particles (FPP) configured to be in contact with said removed sample, said plurality of FPP are further configured to change at least one of their redox properties upon interaction with dissolved molecular oxygen or with "ad hoc" generated radicals of said removed sample;
wherein a change in $T_1$ nuclear relaxation property measured by said MRD is correlated to the presence or concentration of dissolved molecular oxygen or "ad hoc" generated radicals of said removed sample, thereby the redox properties of said production batch or continuous flow of said FBW or of said biological fluid are established.

It is another object of the present invention to disclose the system as defined above, wherein said biological fluid is selected from a group comprising urine, blood, lymph, plasma, cerebrospinal fluid, saliva, amniotic fluid, bile and tears.

It is another object of the present invention to disclose a system for establishing the portability of a production batch or continuous flow of a flowable Foodstuff, Beverage or Wine (FBW), comprising:
a. a magnetic resonance device (MRD) configured to measure a change in nuclear relaxation property of a sample removed from said production batch or continuous flow of said flowable FBW; and,
b. a plurality of functionalized paramagnetic particles (FPP) configured to be in contact with said sample, said plurality of FPP are further configured to change their redox/oxidative properties upon interaction with dissolved molecular oxygen or "ad hoc" generated radicals of said removed sample;
wherein a change in $T_1$ nuclear relaxation property measured by said MRD correlates with dissolved molecular oxygen or "ad hoc" generated radicals concentration of said FBW sample, thereby establishing the potability of said production batch or continuous flow of said flowable FBW.

It is another object of the present invention to disclose the system as defined above, wherein a concentration value lower than about 6 ml of dissolved oxygen per liter of said removed sample is indicative of the potability of said production batch or continuous flow of said FBW.

It is another object of the present invention to disclose the system as defined above, wherein a value lower than X ml of oxygen per liter is correlated to >7 of the 9 point hedonic scale.

It is another object of the present invention to disclose the system as defined above, wherein a value lower than X ml of oxygen per liter is correlated to >y of the hybrid scale.

It is another object of the present invention to disclose the system as defined above, wherein a value lower than X ml of oxygen per liter is correlated to >y of the self-adjusting scale.

BRIEF DESCRIPTION OF THE DRAWINGS

In order to understand the invention and to see how it may be implemented in practice, several embodiments will now be described, by way of non-limiting example only, with reference to the accompanying drawing, in which.

DETAILED DESCRIPTION OF THE INVENTION

Figure 1:
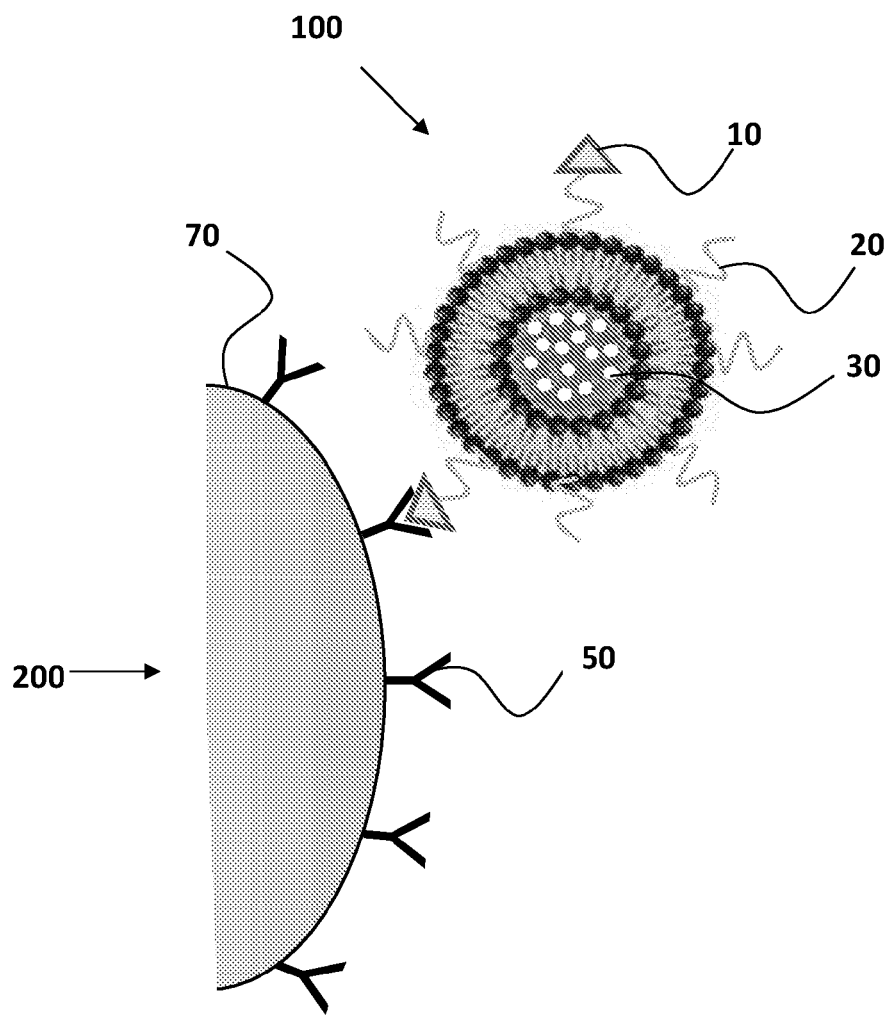
FIG. 1: is a schematic illustration of one embodiment of the system for assessment of cell epitopes, disclosed in the present invention.

The following description is provided, alongside all chapters of the present invention, so as to enable any person skilled in the art to make use of said invention and sets forth the best modes contemplated by the inventor of carrying out this invention. Various modifications, however, will remain apparent to those skilled in the art, since the generic principles of the present invention have been defined specifically to provide a method for detection of a biochemical molecular species in a sample and a system thereof.

Assessment of markers can be pursued by a number of techniques and NMR/MRI is one of them. The detection of a biomarker implies the use of a probe that binds or is responsive to the given biomarker. The probe acts as reporter in the selected NMR/MRI modality. A modality endowed with high sensitivity which is represented by $^1$H-Relaxometry as the measured signal arising from the "bulk" water solvent, is provided by the present invention. By this approach one measures the effect of the responsiveness of the probe on specific properties of the water $^1$H resonance in the presence of the biomarker of interest. $T_1$, $T_2$ and $T_2^*$ are the parameters that may be taken in consideration in the herein provided $^1$H-relaxometric assay.

According to one embodiment, the present invention provides a method for detecting a target biochemical molecular species in a sample, especially a sample whose main component is water, comprising; (a) obtaining a sample; (b) providing Functionalized Paramagnetic Particles (FPP) configured to interact with said target biochemical molecular species, each FPP comprising a paramagnetic core and a moiety configured to interact with said target biochemical molecule or a set of biochemical molecules collectively defining a property of the specimen; (c) contacting said FPP with said sample under conditions that allow the interaction between said FPP and said biochemical molecular species; (d) exposing said sample to an applied magnetic field; and, (e) measuring a change in a nuclear relaxation property of water protons of said sample caused by said interaction between said FPP and said biochemical molecular species, in the applied magnetic field. In a core aspect of the invention, a change in $T_1$ nuclear relaxation property of water protons is correlated to the presence of said target biochemical molecular species in said sample and/or to at least one property associated with the occurrence of said biochemical molecular species in said sample. In a further embodiment of the invention, the FPP comprises a particle made of a non ferrous oxide paramagnetic core.

In a further embodiment, the present invention provides A method for detecting a target biochemical molecular species or at least one property correlated with the occurrence of said biochemical molecular species in a sample whose main component is water, comprising; (a) obtaining a sample whose main component is water; (b) providing Functionalized Paramagnetic Particles (FPP) comprising a paramagnetic core and a moiety configured to interact with said target biochemical molecular species or with molecules collectively reporting on a property of said target biochemical molecular species; (c) contacting said FPP with said sample; (d) exposing said sample to an applied magnetic field; and, (e) measuring a change in a nuclear relaxation property of said sample, caused by said interaction between said FPP and said biochemical molecular species or said molecules collectively reporting on a property of said target biochemical molecular species; in the applied magnetic field; and, (f) correlating said change to the presence of said biochemical molecular species in said sample or to at least one property correlated with the occurrence of said biochemical molecular species in said sample; wherein a change in $T_1$ nuclear relaxation property of the water protons in said sample is correlated to the presence of said target biochemical molecular species or to at least one property correlated with the occurrence of said biochemical molecular species in said sample, further wherein said FPP comprises a non ferrous oxide paramagnetic core.

It is herein disclosed that according to a main embodiment, the present invention uniquely combines NMR relaxometer technology, preferably a portable NMR device, with an amplification procedure for the quantification of a biomarker or biochemical molecule or biochemical molecular species of interest. The present invention provides a novel relaxometric assay based on appropriately designed functionalized paramagnetic particles (FPP), preferably liposomes, containing a paramagnetic core or paramagnetic species and a moiety/moieties, which is/are specifically designed to interact and/or be responsive to the target biomarker or biochemical molecular species or analyte of interest.

The use of paramagnetic species allows determining different concentrations of i.e. a biomarker or analyte of interest within the tested sample, thus affecting for example the assessment between healthy and diseased tissues. Gadolinium (Gd)-based contrast agents are the most used systems. The development of new Gd-based or other metal ion contrast agents with high relaxation enhancement ability and targeting capability is a further aspect of the present invention. It is also within the scope of the present invention to set-up innovative molecular magnetic resonance protocols. These protocols are capable of detecting epitopes that are present at very low concentrations (typically in the 50-100 nmol/L range) and therefore it is necessary to design proper means and methods to amplify the response upon recognition of the target molecule of interest.

According to one aspect, the present invention provides a magnetic resonance-relaxometric assay and system adapted to measure small volume of samples.

According to certain aspects of the present invention, automated systems (i.e. a processor) and procedures are herein provided configured to determining a change in nuclear relaxation properties of a sample containing a target biochemical molecule or biochemical molecular species of interest. These automated systems and procedures are further capable of correlating the measured change in the nuclear relaxation enhancement with the quantification of the target biochemical molecule or biochemical molecular species or an overall property of interest within said sample.

It is further within the scope of the present invention to disclose means and methods for performing quality control of the produced functionalized paramagnetic particles and the $T_1$ measurements that reports on a specific target biomarker or epitope of interest.

It is further within the scope of the present invention to disclose means and methods for detecting at least one property correlated with the occurrence of a biochemical molecular species in a sample.

In a further embodiment of the invention the method as disclosed herein further comprises steps of analyzing at least one characteristic or property of the target molecular species selected from a group comprising concentration, permeability, oxidation state, redox characteristic (reduction-oxidation state), activation state and any combination thereof.

As used herein the term 'plurality' applies hereinafter to any integer greater than or equal to one.

The term 'about' denotes ±25% of the defined amount or measure or value.

The term 'biochemical molecule' as used herein refers to any chemical or biological molecule. Examples of chemical or biological molecules included within the scope of the present invention may comprise, but are not limited to: a protein, a pathogen, a prion, a virus, a bacteria, a contaminant, a pathological isoform, a biomarker, an allergen, a neurotransmitter, an antigenic determinant, an epitope, a cell marker, cell membrane marker or epitope, a membrane marker, an enzyme, a chemical molecule, an analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue and any combination thereof.

The term 'biochemical molecular species' as used herein refers to a biological or chemical molecule as defined above or a set of biochemical molecules, collectively defining a property of a specimen or to one or more biochemical molecules collectively reporting on a given property. It is within the disclosure of the present invention that the term 'biochemical molecular species' refers to biochemical molecules that are substantially similar in their chemical and/or biological properties and their identification and quantification are of interest. In other embodiments, the term 'biochemical molecular species' can be applied to an ensemble or family of chemically or biologically identical molecular entities that can explore the same set of chemical or biological characteristics.

It is still in the scope of the present invention to provide the method as defined above, further comprising steps of selecting the analyte from a group comprising an organic analyte and an inorganic analyte.

The term 'particle' refers hereinafter to any form comprising, but not limited to, a single molecule, a multimeric molecule or system, a macromolecule, a monomer, an oligomer, a polymer, a vesicle, a nano or micro sized vesicle, a liposome, a probe, a cell, a yeast cell or any combination thereof.

The term 'Functionalized Paramagnetic Particle' or 'FPP' refers hereinafter to a particle or probe containing a paramagnetic entity or agent or core and a moiety that is adapted to interact with a target biochemical molecular species or biomarker of interest.

In a preferred embodiment of the invention, the paramagnetic entity, agent, or core constitutes a non ferrous oxide metal ion. According to certain embodiments, the paramagnetic entity, agent, or core comprise a metal ion, including oxides of a metal ion, oxides of a transition metal, mixed oxides of a transition metal and their mixtures. More specifically, the metal ion may be selected from a group comprising an ion of nickel, manganese, copper, gadolinium, dysprosium, europium and mixtures thereof.

In another embodiment of the invention, the FPP may include a moiety or residue adapted to specifically interact with a target biochemical molecular species or biomarker of interest. Such a moiety or residue may comprise a receptor, ligand or any compound, such as a biomolecule or a small molecule, an antibody or an antigen-binding fragment that binds specifically to a selected target molecule or analyte. In specific embodiments, a moiety or residue may comprise a macromolecule, a peptide, a hormone, a fatty acid, a lipid, a receptor agonist and/or antagonist, an amino acid, a sugar, lectins, albumins, polycarbon molecules, glycoproteins, nucleic acids, pegylated molecules, liposomes, chelators, cells, viruses, chemotherapeutic agents, biotin, streptavidin and any combination thereof. In preferred embodiments of the invention, such functional moieties or residues as herein described are configured to confer the FPP with molecular specificity, such that the change in the measured $T_1$ nuclear relaxation property correlates with the presence and/or concentration of the target biochemical molecular species or biomarker of interest or to a collective property of the specimen.

The term 'paramagnetic core' used herein refers hereinafter to a paramagnetic species or paramagnetic payload or paramagnetic entity or paramagnetic agent that may include a metal ion, a metal complex, oxides of a metal ion, oxides of a transition metal, mixed oxides of a transition metal, metal complexes, aggregates of metal complexes, polymer-bound metal complexes, stable organic radicals and their mixtures. The metal ion may be selected from a group comprising an ion of nickel, iron, manganese, copper, gadolinium, europium and mixtures thereof.

The term 'nuclear relaxation property' refers hereinafter to the relaxation of water protons. The effect is a change in magnetic resonance signal, which is measured as a shortening of the longitudinal ($T_1$, spin-lattice) and transverse ($T_2$, spin-spin) relaxation times. In one embodiment, the capacity of the paramagnetic species to decrease $T_1$ and $T_2$ is respectively defined as the transverse and the longitudinal relaxivities. It is herein acknowledged that $T_1$ values are longer at higher field strengths. Furthermore, the $T_1$ parameter is not affected by internal magnetic field gradients or by differences in fluid diffusivity. Moreover, instrument artifacts influence $T_1$ measurements to a much lesser degree than $T_2$ measurements.

Thus, in one aspect, the system and method of the present invention is directed to detecting a biochemical molecule(s) or biochemical molecular species in a sample by measuring a change in the $T_1$ nuclear relaxation property of said sample, operated by an interaction between Functionalized Paramagnetic Particles (FPP) and the biochemical molecular species, in the applied magnetic field. The aforementioned change in $T_1$ nuclear relaxation property is correlated to the presence of said target biochemical molecular species in said sample.

In another aspect, the invention is directed towards novel combinations of $T_1$ and $T_2$ measurements, for example, to detect the presence and/or concentration of a biochemical molecular species or analyte of interest in a sample. In one embodiment, these combinations of $T_1$ and $T_2$ measurements may provide synergistic effects with respect to detection and characterization of a target biochemical molecular species.

The term 'ad hoc generated radicals' as used herein refers to atoms, molecules, or ions with unpaired electrons or an open shell configuration, generated for, or as a result of, a particular or special purpose or end presently under consideration. Because of the unpaired electrons, free radicals are highly chemically reactive. Free radicals may have positive, negative, or zero charge.

According to specific embodiments, the term 'ad hoc generated radicals' relates to detecting generated oxygen-containing radicals using the means and methods as described inter alia for assessing the anti-oxidant properties of a sample of interest.

The term 'correlated to' or 'correlates with' refers hereinafter to either a positive or negative dependence or connection or correspondence between two variables, parameters or sets of data, i.e. between the measured change in nuclear relaxation property of an analysed sample and presence or other characteristic of a target biochemical molecular species within said sample.

The term 'non ferrous oxide' is used hereinafter to indicate metals other than iron and more particularly to oxides of ions that are not iron-based.

The term 'portable' applies hereinafter to any hand held or wearable devices. The device can be carried or worn by the human body on a belt or in a pocket.

The term 'self-fastening' refers hereinafter to a strong magnetic connection between the side-magnets and the cage walls. The magnets' edges are attracted to each other such that a closed form is provided. The cage, magnetically attracted to the side-magnets, supports itself without need for another connection.

The term 'flexi-jointed' refers hereinafter to the geometric arrangement of the cage walls wherein the joints of the walls are separated by an air gap, such that at least a portion of said walls is left free to move and thus, if dislocation of one of the walls occurs, it is able to re-adjust so as to fit with adjacent (sometimes perpendicular) wall. The flexi-jointed walls form the cage in such a manner that at least one of its x, y or z dimensions is adjustable; hence a variation of the cage contour, size or shape, e.g., cross section is obtained.

The term 'superimposed' refers hereinafter to the arrangement of the cage walls; each wall is placed over the other in an overlaying manner.

The term 'magnetic resonance device' (MRD) applies hereinafter to any Magnetic Resonance Imaging (MRI) device, any Nuclear Magnetic Resonance (NMR) spectroscope, any Electron Spin Resonance (ESR) spectroscope, any Nuclear Quadrupole Resonance (NQR), any NMR relaxometer apparatus, or a portable NMR or MRI or any combination thereof.

The term 'tolerance' refers hereinafter to the interval between the corner-magnets and the cage walls, enabling displacement of the walls.

The term 'adjust' applies hereinafter to a change of the magnet's parameters before or after assembly, to optimize the magnetic field uniformity.

The term 'pole-piece' applies hereinafter to an element of high permeability material used to shape the uniformity of the magnetic flux from a permanent magnet.

The term 'side-magnets' applies hereinafter to permanent magnets arranged around the sides of pole-pieces.

The term 'sample imaging units' applies hereinafter to a device adapted to provide a means of measuring the magnetic resonance of a sample within a uniform magnetic field.

The term 'fluid imaging units' applies hereinafter to a device adapted to provide a means of measuring the magnetic resonance of a fluid sample within a uniform magnetic field.

The term 'switching rate' applies hereinafter to the number of separated devices which are activated in a given time period.

The term 'stratificated device' refers hereinafter to any MRD 300 which is characterized by more than two layers, forming more than two detecting volumes, e.g., in a top-and-bottom configuration and/or at least two adjacent feeding streams carrying a plurality of objects in said configuration.

The term 'residue' or 'residues' as used herein refers to any particle or particulate specific to a selected biological or chemical agent. It is within the scope of the present invention that such a residue may include, but it is not limited to a biomarker, a DNA, a protein, a peptide or any other part of a selected biological or chemical agent, particularly a pathogen.

The term 'MRI contrast agents' refers hereinafter in a non-limiting manner to a compound or other substance introduced to the anatomical or functional region being imaged in order to enhance the contrast of structures, due to difference in the apparent density of various organs and tissues. Contrast agents are used in medical imaging studies to make it easier to see the internal structures of the body. The addition of contrast agents in many cases improves sensitivity and/or specificity to improve tissue discrimination in MRI. MRI contrast agents are classified by the different changes in relaxation times after their injection. The most commonly used intravenous contrast agents are based on chelates of gadolinium.

The term 'rapidly' refers herein to a time interval of less than 5 minutes.

The term 'nearly contemporaneously' refers to a time interval less than the time interval between generation of successive first images.

It is thus one embodiment of the present invention to provide, a method for detecting a target biochemical molecular species in a sample, comprising; (a) obtaining a sample; (b) providing Functionalized Paramagnetic Particles (FPP) configured to interact with said target biochemical molecular species of said sample, each FPP comprising a paramagnetic core and a moiety configured to interact with said target biochemical molecular species or a set of biomedical molecules collectively defining a property of the specimen; (c) contacting said FPP with said sample under conditions that allow the interaction between said FPP and said biochemical molecular species or molecules; (d) exposing said sample to an applied magnetic field; and, (e) measuring a change in a nuclear relaxation property of said sample caused by said interaction between said FPP and said biochemical molecular species or molecules, in the applied magnetic field; wherein a change in $T_1$ nuclear relaxation property is correlated to the presence of said target biochemical molecular species in said sample, further wherein said FPP comprises a particle made of a non ferrous oxide paramagnetic core.

It is a further embodiment of the present invention to provide a method for characterizing a target biochemical molecular species in a sample, comprising; (a) providing a sample; (b) providing Functionalized Paramagnetic Particles (FPP) adapted to interact with said target biochemical molecular species, each FPP comprising at least one paramagnetic core and at least one moiety that is adapted to interact with said target biochemical molecular species; (c) contacting said FPP with said sample under conditions that allow the interaction between said FPP and said target biochemical molecular species; (d) exposing said sample to an applied magnetic field; and, (e) measuring a change in a nuclear relaxation property of said sample caused by said interaction between said FPP and said target biochemical molecular species in the applied magnetic field; wherein a change in $T_1$ nuclear relaxation property is correlated to at least one characteristic of said target biochemical molecular species in said sample, further wherein said FPP comprises a non ferrous oxide paramagnetic core or paramagnetic species.

It is further within the scope of the present invention that the analyzed samples are either solid, liquid gas or a combination thereof. Especially, the analyzed sample may comprise a biological fluid, a biological tissue, a tissue extract, an industrial fluid, food sample, a beverage, wine, water and any combination thereof.

More specifically, a biological fluid sample may derived, for example, of urine, blood, plasma, lymph, cerebrospinal fluid, saliva, amniotic fluid, bile and tears.

It is also in the scope of the present invention to provide the method as defined above, further comprising steps of performing two or more measurements to determine the relaxation time of the sample, wherein the measurements are performed before and after at least one addition of said FPP.

It is still in the scope of the present invention to provide the method as defined above, further comprising steps of detecting said target biochemical molecular species and/or characterizing at least one property correlated with the occurrence of said biochemical molecular species in vitro.

It is still in the scope of the present invention to provide the method as defined above, wherein said FPP are formed as a single molecule, a multimeric system, a micro-sized vesicle or particle, a nano-sized vesicle or particle, a liposome, a probe or any combination thereof.

It is still in the scope of the present invention to provide the method as defined above, comprising an additional step of selecting said sample from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

It is still in the scope of the present invention to provide the method as defined above, further comprising steps of selecting said sample from a group comprising a biological fluid, a biological tissue, a tissue extract, an industrial fluid, food sample, a beverage, wine, water, potable water, sewage, irrigation water, sea water, river water, lake water, industrial effluent, farm effluent, effluent from human habitation, road runoff, cleaning fluid, a gas sample or any combination thereof.

It is still in the scope of the present invention to provide the method as defined above, further comprising steps of selecting said biological fluid from a group comprising urine, blood, plasma, lymph, cerebrospinal fluid, saliva, amniotic fluid, bile and tears.

It is still in the scope of the present invention to provide the method as defined above, comprising an additional step of providing said sample within a production process.

It is still in the scope of the present invention to provide the method as defined above, comprising an additional step of selecting said production process in an industrial area, said industrial area is a member of a group consisting of the pharmaceuticals, food production, beverage production, chemical refining, chemical processing, medical products, biological products, metal casting, metal refining, desalination, fluid purification, and sewage processing.

It is still in the scope of the present invention to provide the method as defined above, further comprising steps of analyzing at least one characteristic or property of said target molecular species selected from a group comprising concentration, permeability, oxidation state, redox characteristic (reduction-oxidation state), activation state and any combination thereof.

It is still in the scope of the present invention to provide the method as defined above, further comprising steps of applying a magnetic field, thereby enhancing a change in a paramagnetic nuclear relaxation property of said sample upon comparing relaxation rates at two different magnetic fields.

It is still in the scope of the present invention to provide the method as defined above, further comprising steps of measuring a change in a nuclear relaxation property of said sample using a portable NMR or MRI measuring means.

It is still in the scope of the present invention to provide the method as defined above, further comprising steps of measuring a change in a nuclear relaxation property of said sample using a magnetic resonance device (MRD) consisting of magnets housed within a cage.

It is still in the scope of the present invention to provide the method as defined above, further comprising steps of measuring a change in a nuclear relaxation property of said sample using a self-fastening cage type of a magnetic resonance device (MRD) (300).

According to a further embodiment of the present invention, in a self-fastening cage of a magnetic resonance device (MRD) (300), a method as defined above further comprises steps of providing a homogeneous, stable and uniform magnetic field therein, further wherein said self-fastening cage type MRD additionally characterized by an outside shell comprising at least three flexi-jointed superimposed walls (1).

According to a further embodiment of the present invention, in a self-fastening cage type MRD (300), a method as defined above further comprises steps of providing an MRD characterized by an outside shell; said outside shell comprising at least three flexi-jointed superimposed walls (1) disposed in a predetermined clockwise or counterclockwise arrangement; said MRD comprising: (a) at least six side-magnets (2) arranged in two equal groups being in a face-to-face orientation in a magnetic connection with said outside shell, increasing the overall strength of the magnetic field provided in said cage; (b) at least two pole-magnet pieces (3), arranged in a face-to-face orientation in between said side-magnets (2); (c) at least two main-magnets (4), located on said pole-pieces (3), arranged in a face-to-face orientation, generating the static magnetic field therein said cage; and, (d) shimming mechanism, said mechanism is selected from a group consisting of an array of active shim coils, passive shimming elements or a combination thereof; wherein at least a portion of said side-magnets (2) are superconductors or ferromagnets.

It is further in the scope of the present invention to provide a magnetic resonance device (MRD) comprising: a means of producing a large, uniform magnetic field around a sample, such as a large permanent magnet and shimming mechanism selected from active or passive shimming elements; a means of producing a magnetic field gradient around the sample; and a magnetic resonance sensing probe comprising an inductance coil and capacitor connected to a radio antenna.

It is still in the scope of the present invention to provide the method as defined above, wherein said applied magnetic field comprises a magnetic resonance signal level in the range of about 0.1 Tesla and about 10 Tesla.

It is still in the scope of the present invention to provide the method as defined above, further comprises steps of applying a magnetic resonance frequency in the range of about 5 MHz to about 40 MHz.

It is still in the scope of the present invention to provide the method as defined above, comprising an additional step of providing a magnetic resonance device adapted to producing high contrast high resolution images of said sample.

It is still in the scope of the present invention to provide the method as defined above, comprising an additional step of providing a magnetic resonance device comprising: (a) an envelope for least partially confining said sample; (b) a plurality of magnets located at least partially around said envelope; and, (c) a CPU to process said images comprising a computer readable medium containing instructions for generating at least one third image superimposing at least one image of said first images with at least one image of said second images. In a specific embodiment, the plurality of magnets comprising: (a) a least one first magnet configured to provide a high magnetic field for generating multiple time-resolved one or more first images at high resolution of at least a portion of said sample; and (b) a least one second magnet configured to provide a low magnetic field for generating multiple time-resolved one or more second images at high contrast of at least portion of same said sample; wherein at least one image of said first images and at least one image of said second images being generated in a time no greater than approximately the time between two first images.

It is still in the scope of the present invention to provide the method as defined above, comprising additional steps of: (a) generating multiple time resolved one or more first images at high resolution of at least a portion of said sample; (b) generating multiple time resolved one or more second images at high contrast of at least portion of same said sample; and (c) superimposing at least one image of said first images with at least one image of said second images; whereby a high-contrast, high resolution real-time continuous image of said sample is obtained.

It is still in the scope of the present invention to provide the method as defined above, comprising an additional step of selecting said at least one first magnet to be of 2 Tesla and lower.

It is still in the scope of the present invention to provide the method as defined above, comprising an additional step of selecting said at least one first magnet to be of 2 Tesla and higher.

It is still in the scope of the present invention to provide the method as defined above, comprising an additional step of selecting said at least one first magnet from a group consisting of permanent magnets, electromagnets, superconducting magnets, and any combination thereof.

It is still in the scope of the present invention to provide the method as defined above, comprising an additional step of selecting said at least one second magnet to be of 2 Tesla and lower.

It is still in the scope of the present invention to provide the method as defined above, comprising an additional step of selecting said at least one second magnet to be of 2 Tesla and higher.

It is still in the scope of the present invention to provide the method as defined above, comprising an additional step of selecting said at least one second magnet from a group consisting of permanent magnets, electromagnets, superconducting magnets, and any combination thereof.

It is still in the scope of the present invention to provide the method as defined above, comprising an additional step of selecting said magnets from a group consisting of permanent magnets, electromagnets, superconducting magnets, and any combination thereof.

It is still in the scope of the present invention to provide the method as defined above, further comprising steps of selecting said moiety from a group comprising antibodies, antibody fragments, monoclonal antibody, receptors, ligands, macromolecules, peptides, hormones, fatty acids, lipids, receptor agonists and antagonists, amino acids, sugars, lectins, albumins, polycarbon molecules, glycoproteins, nucleic acids, pegylated molecules, liposomes, chelators, cells, viruses, chemotherapeutic agents and any combination thereof.

It is still in the scope of the present invention to provide the method as defined above, further comprising steps of detecting and/or analysing a target molecular species selected from a group comprising a biological molecule, a chemical molecule, an analyte, a contaminant, a particle, a pathogen or any combination thereof.

It is still in the scope of the present invention to provide the method as defined above, further comprising steps of selecting said target biochemical molecular species from a group comprising a protein, a pathogen, a prion, a virus, a bacteria, a contaminant, a pathological isoform, a biomarker, an allergen, a neurotransmitter, an antigenic determinant, an epitope, a cell marker, cell membrane marker or epitope, a membrane marker, an enzyme, a chemical molecule, an analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue and any combination thereof.

It is still in the scope of the present invention to provide the method as defined above, further comprising steps of selecting said analyte from a group comprising an organic analyte and an inorganic analyte.

It is still in the scope of the present invention to provide the method as defined above, wherein said inorganic analyte is molecular oxygen or an oxygen-containing molecule or oxygen containing radicals and combinations thereof.

It is still in the scope of the present invention to provide the method as defined above, comprising an additional step of detecting oxygen-containing radicals "ad hoc" generated, for assessing the anti-oxidant properties of the sample.

It is still in the scope of the present invention to provide the method as defined above, wherein said paramagnetic core is a metal ion, oxides of a metal ion, oxides of a transition metal, mixed oxides of a transition metal and their mixtures.

It is still in the scope of the present invention to provide the method as defined above, further comprising steps of selecting said metal ion from a group comprising an ion (except for iron oxide) of nickel, manganese, copper, gadolinium, dysprosium, europium and mixtures thereof.

It is still in the scope of the present invention to provide the method as defined above, further comprising steps of selecting said paramagnetic core or species loaded in the FPP from a group comprising metal complexes, aggregated of metal complexes, polymer-bound metal complexes, stable organic radicals and mixtures thereof.

It is still in the scope of the present invention to provide the method as defined above, based on a competition assay for assessing oxygen consumption or redox characteristics, comprising steps of detecting differences in Paramagnetic Relaxation Enhancement (PRE) properties induced by a change in at least one redox characteristic of said FPP, using an applied magnetic field.

It is still in the scope of the present invention to provide the method as defined above, further comprises steps of selecting said redox characteristic from a group comprising lipid peroxidation, lipid peroxidation followed by a change in membrane permeability, redox potential of metal ions, formation and cleavage of disulfide bonds, oxidation state, antioxidant activity and any combination thereof.

It is still in the scope of the present invention to provide the method as defined above, further comprises a step of providing said FPP as a liposome loaded with a plurality of paramagnetic cores or payloads.

It is still in the scope of the present invention to provide the method as defined above, further comprising steps of applying a magnetic field, thereby enhancing a change in the permeability of said liposome so as to affect a nuclear relaxation property of said sample.

It is still in the scope of the present invention to provide the method as defined above, further comprising steps of applying a magnetic field, thereby enhancing a change in at least one of cleavage or formation of disulfide bonds of said moiety so as to affect a nuclear relaxation property of said sample.

It is still in the scope of the present invention to provide the method as defined above, further comprising steps of applying a magnetic field, thereby affecting at least one property of said FPP selected from a group comprising concentration, lipid peroxidation, membrane permeability, redox potential, formation and cleavage of disulfide bonds, oxidation state, redox potential, activation state, binding affinity, and any combination thereof, so as to induce a change in a nuclear relaxation property of said sample.

It is still in the scope of the present invention to provide the method as defined above, further comprises steps of conjugating said liposome with a site-specific ligand.

It is still in the scope of the present invention to provide the method as defined above, further comprises steps of conjugating said liposome with a biotin activated molecule.

It is still in the scope of the present invention to provide the method as defined above, further comprises steps of providing said FPP as a biotinylated liposome.

According to a further embodiment, the present invention provides a method for detection of a biomarker in a sample whose main component is water, comprising steps of: (a) obtaining a sample; (b) providing liposomes loaded with a plurality of paramagnetic agents, said liposomes are conjugated with a site specific moiety configured to interact with said biomarker in said sample; (c) contacting said liposomes with said sample under conditions that allow the interaction between the site specific moiety and said biomarker; (d) exposing said sample to an applied magnetic field; and, (e) measuring a change in a nuclear relaxation property of said sample caused by said interaction between the liposomes and said biomarker in the applied magnetic field; wherein a change in $T_1$ nuclear relaxation property is correlated to the presence of said biomarker in said sample.

It is still in the scope of the present invention to provide the method as defined above, further comprises the steps of: (a) providing biotinylated liposomes; said liposomes loaded with a plurality of paramagnetic agents; (b) providing biotinylayed ligands, said ligands configured to interact with said biomarker; (c) providing activated avidin molecules; (d) contacting said biotinylated liposomes, said biotinylayed ligands and said activated avidin molecules with said sample so as to enable avidin-biotin interaction, thereby forming complexes comprising said liposomes, said ligand and said biomarker; such that said complexes are specific to said biomarker; and, (e) measuring a change in a nuclear relaxation property of said sample caused by said complex formation in the applied magnetic field; wherein a change in $T_1$ nuclear relaxation property is correlated to the presence of said biomarker in said sample.

In a further embodiment, the present invention provides a system for detecting a target biochemical molecular species or at least one property correlated with the occurrence of said biochemical molecular species in a sample, especially a sample whose main component is water, said system comprising; (a) a magnetic resonance device (MRD) configured to measure a change in nuclear relaxation property of said sample; and, (b) a plurality of Functionalized Paramagnetic Particles (FPP) configured to interact with said target biochemical molecular species of said sample, each of said FPP comprising a paramagnetic core and a moiety configured to interact with said target biochemical molecular species, or with molecules collectively reporting on a property of said target biochemical molecular species; wherein a change in $T_1$ nuclear relaxation property measured by said MRD is correlated to the presence of said FPP and said biochemical molecular species and/or at least one property correlated with the occurrence of said biochemical molecular species in said sample, thereby detecting the presence of said target biochemical molecular species in said sample, further wherein said FPP comprises a non ferrous oxide paramagnetic core.

In a further embodiment the present invention provides a use of Functionalized Paramagnetic Particles (FPP) configured to interact with a predetermined target biochemical molecular species or a biomarker within a sample, to detect the presence or at least one other characteristic of said target biochemical molecular species or biomarker, each of said FPP comprising a paramagnetic core and a moiety configured to interact with said target biochemical molecular species or with molecules collectively reporting on a property of said target biochemical molecular species; wherein a change in $T_1$ nuclear relaxation property measured by a generated applied magnetic field is correlated to the presence or at least one other characteristic of said target biochemical molecular species in said sample.

In a further embodiment, the present invention provides a method of establishing the redox potential of a production batch or continuous flow of a Foodstuff, Beverage or Wine (FBW), or of a biological fluid, comprising the steps of: (a) obtaining a sample removed from said production batch or continuous flow of said FBW or from a biological fluid; (b) providing Functionalized Paramagnetic Particles (FPP) configured to change their redox potential upon interaction with dissolved molecular oxygen or to active radicals "ad hoc" generated in said removed sample; (c) contacting said FPP with said removed sample; (d) exposing said removed sample to an applied magnetic field; and, (e) measuring a change in a nuclear relaxation property of said removed sample caused by said change in the redox potential or antioxidant properties of said FPP in the applied magnetic field; wherein a change in $T_1$ nuclear relaxation property is correlated with the concentration of said molecular oxygen or of radicals of said removed sample, thereby establishing the redox potential or the anti-oxidant ability of said production batch or continuous flow of said FBW or of said biological fluid.

It is also within the scope of the present invention to provide the method as described above, further comprising the step of providing said FPP conjugated with at least one moiety configured to interact with dissolved molecular oxygen on the "ad hoc" generated radicals.

It is still within the scope of the present invention to provide the method as described above, further comprising the step of selecting said moiety from a group comprising a lipid, a fatty acid, an amino acid, a peptide, a protein, a molecule containing at least one disulfide bond, a liposome and any combination thereof.

It is still within the scope of the present invention to provide the method as described above, further comprising the step of measuring a change in a nuclear relaxation property of said sample caused by a change in the antioxidant activity of said removed sample in the applied magnetic field.

It is still within the scope of the present invention to provide the method as described above, further comprising the step of measuring a difference in Paramagnetic Relaxation Enhancement (PRE) property of said removed sample caused by said interaction of said FPP with said dissolved molecular oxygen or said "ad hoc" generated radicals.

It is still within the scope of the present invention to provide the method as described above, further comprising the step of contacting said removed sample with FPP configured to form a liposome structure, said FPP comprising a paramagnetic core and a fatty acid moiety, wherein peroxidation of said fatty acid moiety substantially changes the permeability of said liposome.

It is still within the scope of the present invention to provide the method as described above, further comprising the step of measuring a change in a nuclear relaxation property of said removed sample based on competition for molecular oxygen consumption.

It is still within the scope of the present invention to provide the method as described above, further comprising the step of contacting said removed sample with FPP comprising a metal ion, oxides of a metal ion, oxides of a transition metal, mixed oxides of a transition metal and their mixtures or paramagnetic species.

It is still within the scope of the present invention to provide the method as described above, further comprising steps of selecting said metal ion from a group comprising an ion of nickel, manganese, copper, gadolinium, dysprosium, europium and mixtures thereof.

It is a further embodiment of the present invention to provide a system for establishing the redox potential of a production batch or continuous flow of a Foodstuff, Beverage or Wine (FBW), comprising: (a) a magnetic resonance device (MRD) configured to measure a change in a nuclear relaxation property of a sample removed from said production batch or continuous flow of said FBW; and, (b) a plurality of Functionalized Paramagnetic Particles (FPP) configured to be in contact with said removed sample, said plurality of FPP are further configured to change their redox potential upon interaction with dissolved molecular oxygen of said removed sample; wherein a change in $T_1$ nuclear relaxation property measured by said MRD is correlated to the concentration of dissolved molecular oxygen of said removed sample of said production batch or continuous flow of said FBW, thereby establishing the oxidative state of said production batch or continuous flow of said FBW.

It is a further embodiment of the present invention to provide a system for establishing the potability of a production batch or continuous flow of a flowable Foodstuff, Beverage or Wine (FBW), comprising: (a) a magnetic resonance device (MRD) configured to measure a change in nuclear relaxation property of a sample removed from said production batch or continuous flow of said FBW; and, (b) a plurality of functionalized paramagnetic particles (FPP) configured to be in contact with said sample, said plurality of FPP are further configured to change their redox potential upon interaction with dissolved molecular oxygen or the "ad hoc" generated radicals of said removed sample; wherein a change in $T_1$ nuclear relaxation property measured by said MRD correlates with dissolved molecular oxygen or the "ad hoc" generated radical concentration of said FBW sample, thereby establishing the potability of said production batch or continuous flow of said FBW.

It is herein acknowledged that the anti-oxidant ability in wine, beverage, foodstuff or in biological fluids changes over time because the oxygen and oxygen contained species are used in oxidative reactions. Thus according to specific embodiments of the invention, the system of the present invention is further adapted to establish the anti-oxidant properties of a foodstuff, wine, beverage or biological fluid sample.

It is further within the scope of the present invention that the term 'hedonic scale' refers to a commonly used and acceptable scale used in food science, marketing research and tasting panels where the respondents indicate the extent to which they either like or dislike food or beverage. The hedonic scale is often used for assessing the quality of wine. Hedonic scales commonly range from 2 (like, dislike) to 7 points. It is reported that commonly, an average person is able to reliably distinguish between no more than 7-9 degrees of perfection of quality trait. One example of such a scale is the five-point hedonic scale, which include the following degrees: like very much, like, is acceptable, do not like, strongly do not like. The hedonic scale is a universal scale, which is used in the determination of the degree of perfection of the assessed elements of quality, as well as clarifying the views of consumers about the quality of the product.

It is also within the scope of the present invention to provide the system as defined above, wherein a value lower than X ml of Oxygen per liter is correlated to >7 of the 9 point hedonic scale.

It is also within the scope of the present invention to provide the system as defined above, wherein a value lower than X ml of Oxygen per liter is correlated to >y of the hybrid scale.

It is also within the scope of the present invention to provide the system as defined above, wherein a value lower than X ml of Oxygen per liter is correlated to >y of the self-adjusting scale.

In a further embodiment, the system and method of the present invention is applicable for assessment of anti-oxidant property of a sample of interest. Such a sample may be derived of a biological fluid, a biological tissue, a tissue extract, an industrial fluid, food sample, a beverage, wine, water, a gas sample or any combination thereof.

According to certain aspects, the anti-oxidant property may be assessed by measuring the redox characteristics of a sample i.e. detecting and quantifying ad hoc generated radicals. For this end paramagnetic particles i.e. FPP comprising a paramagnetic agent linked to a molecular probe may be used.

One optional approach to evaluate the redox characteristics of a sample using the method and system of the present invention is by measuring the lipid peroxidation activity or properties of the sample. This can be achieved by using a paramagnetic probe or FPP comprising a paramagnetic species i.e. Gd which is functionalized with a covalently linked fatty acid moiety i.e. linolenic acid. The transformation of the redox characteristics of the fatty acid moiety may be followed by a T1 change. Such a magnetic resonance effect may reflect the differences in Paramagnetic relaxation enhancement (PRE) property caused by the interaction of the sample with the macromolecular paramagnetic system.

According to an alternative approach, the paramagnetic probe i.e. comprising a Gd entity linked to a fatty acid moiety is a part of a liposome structure. In such a case, the peroxidation of the fatty acid moiety may change the permeability of the liposome membrane and thus affect the measured nuclear relaxation property of the sample.

According to yet another embodiment, the assessment of anti-oxidant property of a sample of interest may be performed using methods based on competition for oxygen consumption or redox characteristics. In such an example the FPP complex as disclosed herein above may contain a metal ion such as Mn(II) as a paramagnetic species, that upon interaction with hyperoxide or superoxide radicals transforms its oxidation state i.e. to Mn (III). The change in the oxidation state of the paramagnetic species may generate T1 effect in $^1$H-relaxometric assay measured by NMR or MRI technique. According to yet another embodiment, the anti-oxidant property of a sample of interest may be assessed using a paramagnetic (i.e. Gd) complex where the measured T1 is dependent on the formation and cleavage of disulfide (s-s) bonds within the functionalized macromolecular probe linked to the paramagnetic moiety.

Reference is now made to FIG. 1 showing a schematic representation of a system and procedure, for detection of a predetermined epitope or receptor, on a cell membrane, using the targeted functionalized paramagnetic particles or probes (FPP) of the present invention. Such a system and method can be useful, for example, for assessment of folate receptors within a biological sample. In this figure, the paramagnetic probe is a liposome 100 loaded with a plurality of paramagnetic species or cores 30. In this embodiment, the liposome 100 is conjugated with a target moiety 10 through a spacer 20, which may comprise for example a pegylated chain. The target moiety 10 can be a ligand (i.e. folic acid or a folic acid derivative) that is adapted to interact or bind with its corresponding receptor 50 (i.e. folate receptor) that may be located on the cellular surface or membrane 70 of a cell 200. The target moiety 10 is allowed to bind with the receptor 50 and the non bound liposomes are then removed. The sample, which includes the bound liposomes loaded with paramagnetic species, is exposed to an applied magnetic field configured to measure a change in nuclear relaxation property of the sample. The change in the measured $T_1$ nuclear relaxation property in the applied magnetic field indicates the presence of the specific receptor in the analysed sample. Furthermore, the difference in the measured Paramagnetic Relaxation Enhancement (PRE) properties is correlated with the concentration of the receptor within the tested sample.

According to a further embodiment, the paramagnetic core 30, embedded within the liposome membrane, comprise Mn(II) ions. In a specific example, each liposome is loaded with about $4*10^5$ Mn(II) ions. In a further embodiment, the target moiety 10, which is conjugated to the liposome membrane, is folate. In such an example, about $9*10^5$ folate residues are exposed per liposome. In a cell binding experiment using Human Ovarian Cancer cells (IGROV-1) overexpressing folate receptors 50 at the cell membrane 70, about 5000 liposomes were found to be bound to each cell. In such an embodiment, the total cell surface is covered by liposomes, thus it is difficult to discriminate between cells with different receptor expression level.

Figure 2:
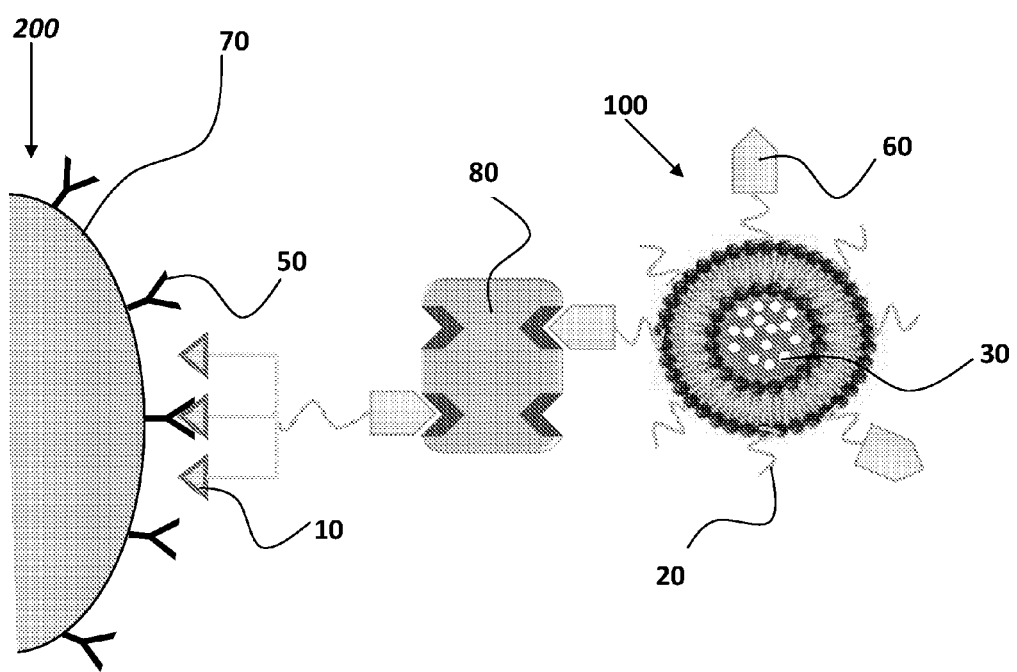
FIG. 2: is a schematic illustration of a further embodiment of the system for assessment of cell epitopes, disclosed in the present invention.

Reference is now made to FIG. 2 showing schematic representation of a multi step procedure, using the functionalized paramagnetic particles or probes of the present invention, for detection of a predetermined epitope or receptor, on a cell membrane. In such an embodiment, biotinylated liposomes 100 are prepared, containing about $10^5$ paramagnetic centers 30 per liposome and biotin residues 60 conjugated with the liposome membrane by a spacer 20. The biotinylated liposomes are added to a sample containing cells 200 expressing folate receptors 50 at their membrane surface 70, activated streptavidin molecules 80, and folic acid residues 10 linked to biotin residues 60. The site specific residues (i.e. biotin-streptavidin and folic acid residues-folate receptors) are allowed to specifically bind to each other and a subsequent washing step of unbound residues is followed. The sample containing the bound paramagnetic liposomes is then exposed to a magnetic field and a change in a nuclear relaxation property (i.e. T1 and/or T2) of the sample is measured. The aforementioned change in a nuclear relaxation property (i.e. T1 and/or T2) of the sample is correlated with the presence and/or concentration of the target molecule, for example the expressed folate receptors on a cellular membranes.

It is thus one embodiment of the present invention to provide an efficient self-fastening cage of a MRD (300) for providing a homogeneous, stable and uniform magnetic field therein, characterized by an outside shell comprising at least three flexi-jointed superimposed metal alloy walls (1).

It is also in the scope of the present invention to provide the aforementioned MRD further comprising at least six side-magnets (2) arranged in two equal groups configured in a face-to-face orientation, in a magnetic connection with the cage walls (1), increasing the overall strength of the magnetic field provided in said cage; at least two pole-pieces (3), arranged in a face-to-face orientation in between side-magnets (2); and, at least two main-magnets (4), located on said pole-pieces (3), arranged in a face-to-face orientation, generating the static magnetic field therein said cage.

Figure 7:
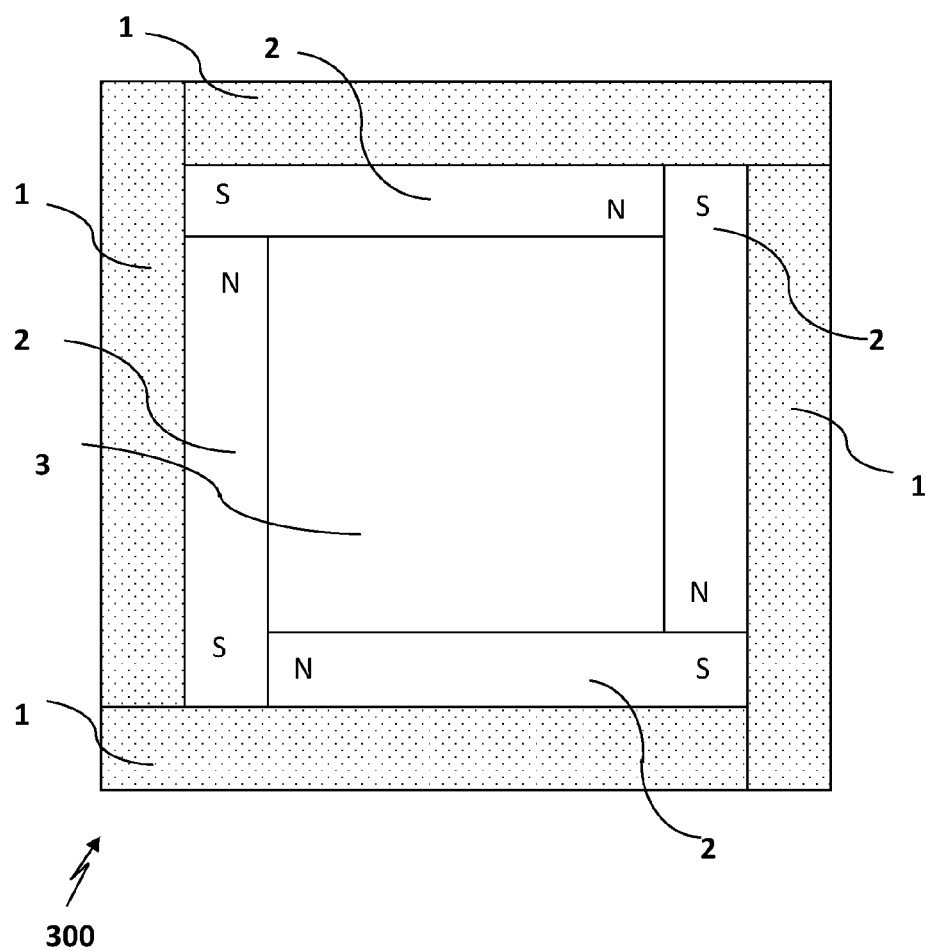
FIG. 7: schematically presents a partial sectional top and out of scale view, with respect to an axial plane of the MRD (300) wherein the shape of a square parallelepiped is provided, having four cage walls (1), four side magnets (2); and a pole-piece (3); said cage walls and side-magnets are essentially interconnected in a superimposed manner such that a self-fastening cage is obtained.

Reference is made now to FIG. 7, schematically presenting a partial sectional top and out of scale view, with respect to an axial plane of the 3D MRD (300) wherein the shape of a square parallelepiped is provided, having four cage walls (1), four side magnets (2); and a pole-piece (3); said cage walls and side-magnets are essentially interconnected in a superimposed manner such that a self-fastening cage is obtained.

Figure 8:
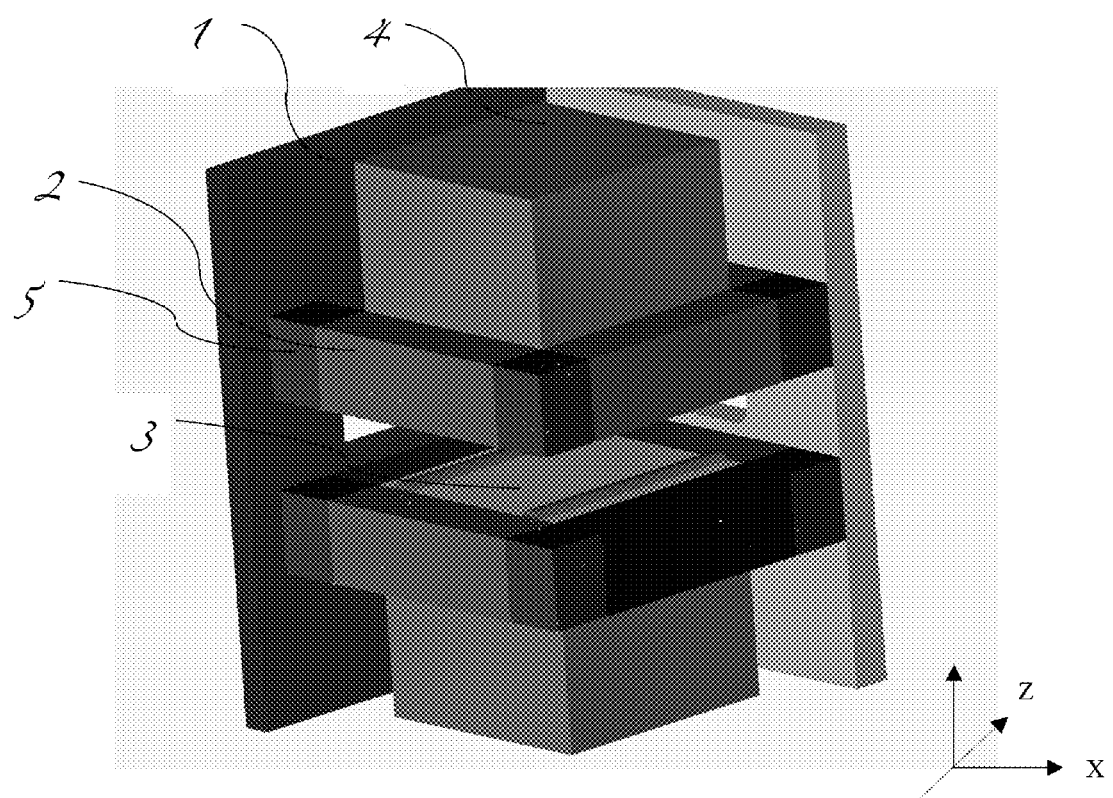
FIG. 8: schematically presents an entire perspective view of the of the 3D MRD (300), having two cage walls (1), eight side magnets (2); two pole-pieces (3); two main magnet (4) and eight square corner-magnets (5) and four cylinder corner-magnets located inside the pole-pieces; all of them are arranged in two equal groups face-to-face orientation; and, FIG. 9: schematically illustrates an embodiment with a high contrast, high resolution magnetic resonance device.
Figure 9:
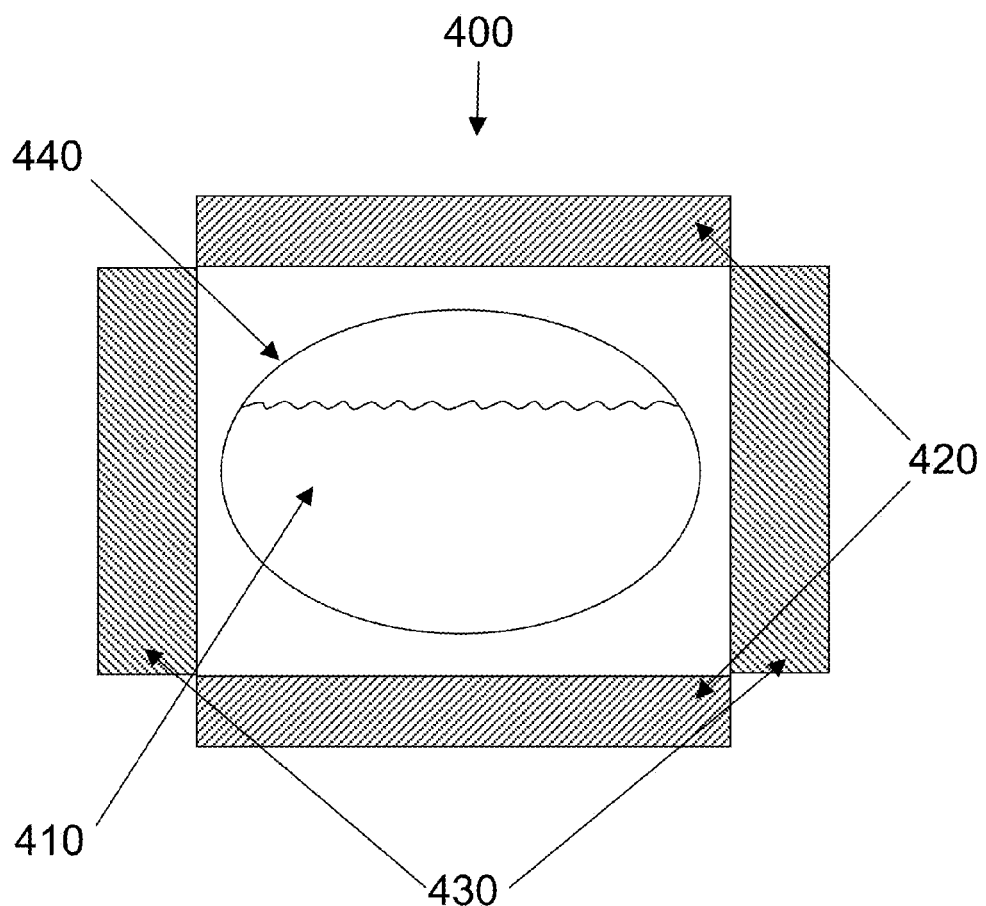

Reference is made now to FIG. 8, schematically presenting an entire perspective view of the of the 3D MRD, having two cage walls (1), eight side magnets (2); two pole-pieces (3); two main magnet (4) and eight square corner-magnets (5) and four cylinder corner-magnets located inside the pole-pieces; all of them are arranged in two equal groups face-to-face orientation.

Figure 4:
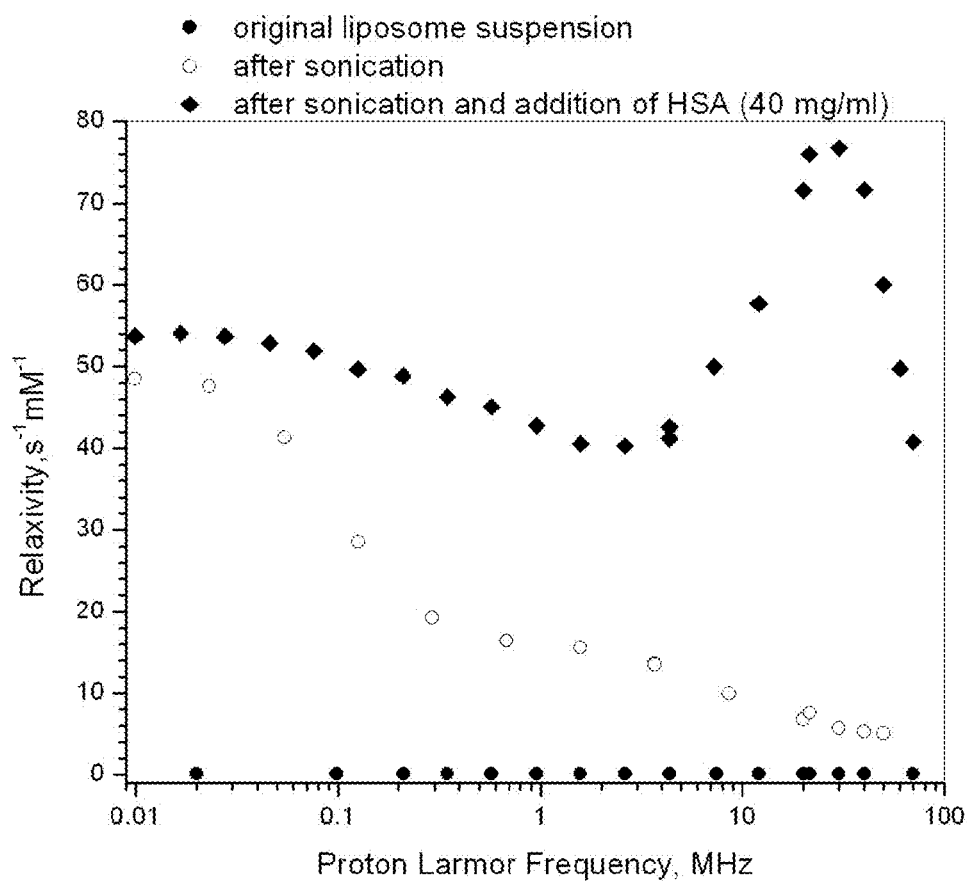
FIG. 4: is a graphic representation of relaxivity results at different proton larmor frequencies.

In another embodiment, a high contrast, high resolution magnetic resonance device i.e. MRI is provided. A non-limiting example of an embodiment of this type is schematically illustrated in FIG. 4. The device (400) comprises two sets of magnets (420, 430). The RF coils (not shown) are part of an envelope (440) which contains the sample to be analyzed (410). In this embodiment, the high magnetic field magnets (420) are in a horizontal orientation, while the low magnetic field magnets (430) are in a vertical orientation. In other embodiments, the low field magnets can be inside the high magnetic field magnets. In yet other embodiments, the low magnetic field magnets can be outside the high magnetic field magnets. Such embodiments can be used in the methods and systems as disclosed herein.

EXAMPLES

Various examples were carried out to prove the embodiments claimed in the present invention. Some of these experiments are referred hereinafter. The examples describe the manner and process of the present invention and set forth the best mode contemplated by the inventors for carrying out the invention, but are not to be construed as limiting the invention.

Example 1

Assessment of Anti-Oxidant Activity (AOA) in Liquid or Beverage Samples, Such as Wine or Spirits or Liquors It is herein acknowledged that AOA prevents lipid peroxidation. In this embodiment, the paramagnetic-probe complex that is used, contains a Gd paramagnetic core that is functionalized with a linoleinic acid moiety (L). Upon interaction of the GD complex (GD-L), with oxygen-based radicals, lipid peroxide products are produced, as schematically shown in the following reaction:

Gd-L→Gd-LO2.→products

The aforementioned lipid transformation process can be followed by T1-change, which may exploit and reflect differences in Paramagnetic Relaxation Enhancement (PRE) upon interaction with the macromolecular paramagnetic complex system.

In an alternative embodiment, Gd-L is part of a liposome structure; the peroxidation of L changes the permeability of the liposome membrane and thus affects the measured $T_1$ nuclear relaxation property of the sample.

In an alternative embodiment, competition assays for oxygen consumption and/or redox characteristics are used, based on the system and method as herein described. Such systems may comprise a Mn(II)-containing paramagnetic probe that transforms into a Mn(III) complex. This transformation may result a T1 nuclear relaxation property effect. In a further example, such a system may comprise a Gd macromolecular complex or probe, where T1 is dependent on the formation and/or cleavage of disulfide (S—S) bonds within the macromolecular probe.

Example 2

Assessment of Epitopes on Cell Membranes

Figure 3:
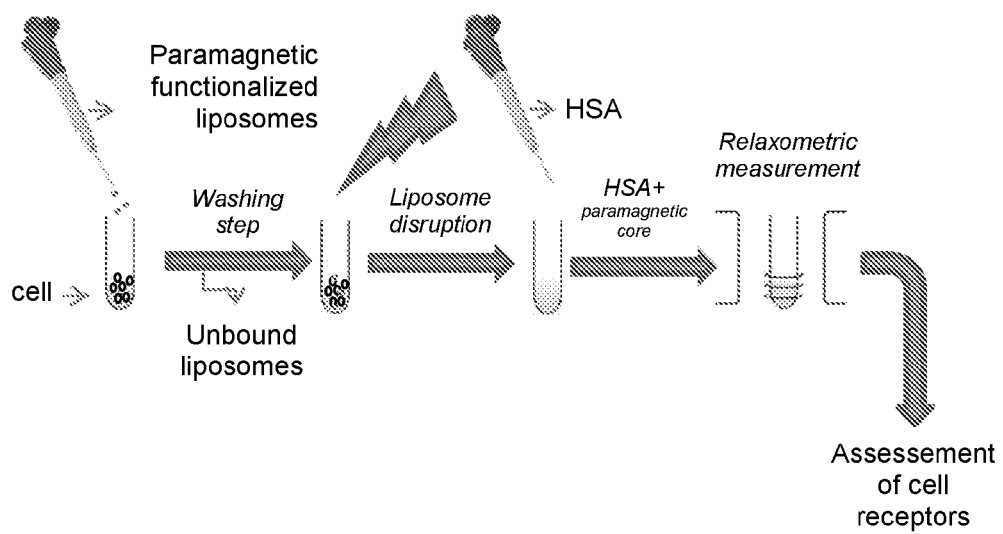
FIG. 3: is a schematic diagram illustrating steps for assessment of cell receptors according to an embodiment of the present invention.

Reference is now made to FIG. 3 schematically describing a further embodiment of the method for assessment of cell receptors using the functionalized paramagnetic particles (FPP) of the present invention. In this embodiment, paramagnetic functionalized liposomes, for example paramagnetic particles as described in FIG. 1 or FIG. 2, are incubated with a sample containing cells suspected to express a receptor of interest. Following a washing step of unbound liposomes, disruption of the bound liposome sample, for example by a sonication procedure, is performed. In a further specific embodiment, Human Serum Albumin (HSA) (about 40 mg/ml) is added to the disrupted cell sample containing the suspended paramagnetic cores. A relaxometric measurement is then performed for determining PRE properties of the sample. The change in PRE as compared with a control sample indicates the presence and/or concentration of the tested target epitope, for example a cell receptor.

Reference is now made to FIG. 4 showing a graphic representation of the relaxometric measurement results over extended range of frequencies (MHz). As can be seen, after sonication and addition of HSA (40 mg/ml) to the sample containing cells expressing a specific epitope and functionalized paramagnetic liposomes adapted to interact with the epitope, as described above, a specific peak in the relaxativity value was shown in the rage of frequencies of about 20-40 MHz.

Figure 5:
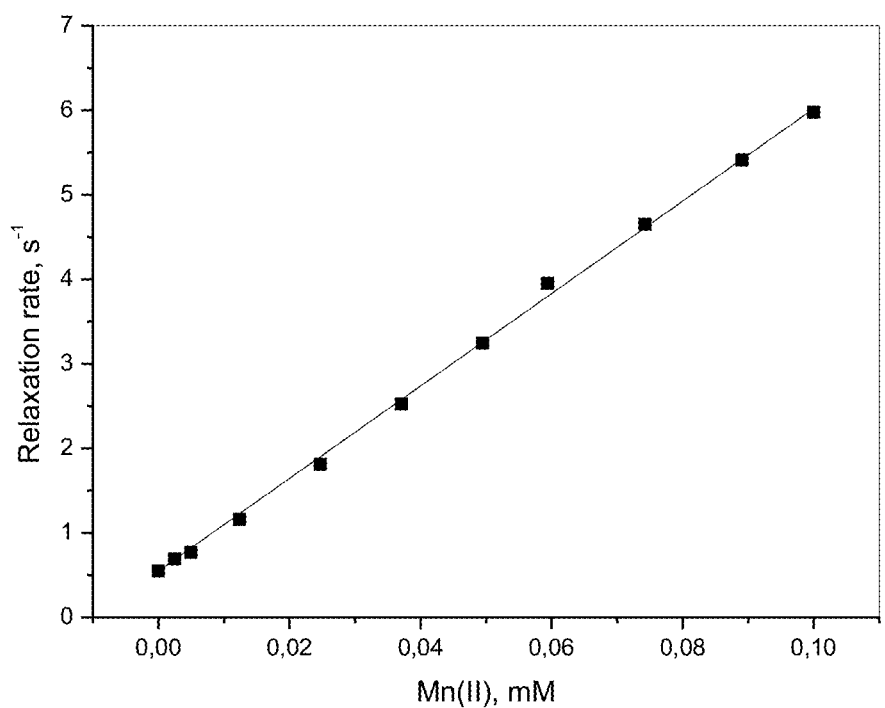
FIG. 5: is a graphic representation showing relaxation rate by Mn(II) ion concentration.

In order to evaluate the affect of the concentration of the paramagnetic agent used in the FPP, samples containing different Mn(II) ion concentration, undergone liposome sonication and HSA (40 mg/ml) addition, were exposed to electromagnetic frequencies of 20 MHz and were subjected to a relaxometric measurement. Reference is now made to FIG. 5, showing a graphic representation of relaxation rate measurement results at different Mn(II) ion concentration. As can be seen in this figure, a direct correlation was observed between concentrations of the paramagnetic core (i.e. Mn(II) ions) used within the FPP, and the measured relation rate. It can be further concluded that a value of about 5 µM Mn concentration was the lowest detectable Mn(II) ion concentration.

The above described experiment shows that Mn(II) ion concentration of [Mn]=5 mM corresponds to $1.5 \times 10^9$ liposome particles in 200 µl. In one embodiment, the number of liposome particles (FPP) is calculated according to the following equation:

No. of receptors per cell×No of cells $\geq 1.5 \times 10^9$

Thus, in the case of $1 \times 10^6$ receptors per cell, 1500 cells are necessary to enable detection of a desirable expressed receptor using the minimal required concentration of Mn(II) ions containing paramagnetic liposomes.

Example 3

Paramagnetic Liposome Preparation

According to certain embodiments of the present invention, functionalized paramagnetic liposome particles are prepared. The $1^{st}$ step of the process may include the preparation of thin lipidic film. In one embodiment, the film comprises the following ingredients (20 mg/ml):

| | |
|---|---|
| DPPC | 77% |
| Cholesterol | 20% |
| DSPE-methoxy-PEG2000 | 2% |
| DSPE-target moiety (i.e.folate)-PEG2000 | 1% |

Figure 6:
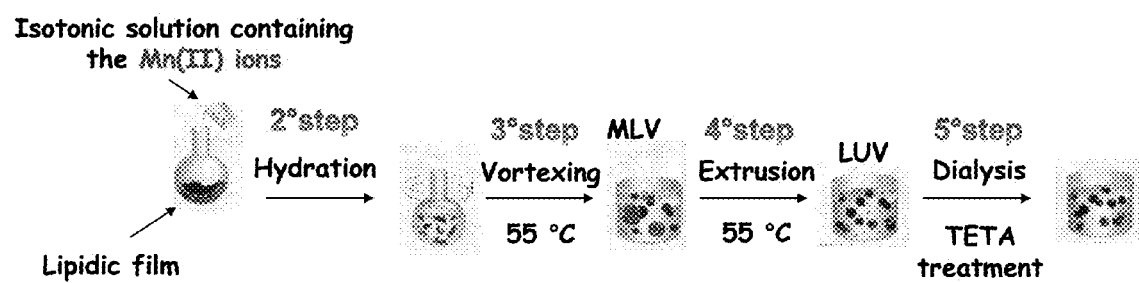
FIG. 6: is a schematic illustration of a process for preparation of paramagnetic liposomes according to an embodiment of the present invention.

Reference is now made to FIG. 6 schematically describing optional steps in the functionalized paramagnetic liposome (FPP) preparation process. In one embodiment, the $2^{nd}$ step of the process includes the mixing of the lipidic film with an isotonic solution containing the Mn(II) ions and the hydration of the mixture. In the $3^{rd}$ step, multilamellar vesicles (MLV) are prepared by vortexing the hydrated mixture at 55° C. This step is followed by a $4^{th}$ step of extrusion at 55° C. to obtain large unilamellar vesicles (LUV) with a mean diameter of above 50 nm, preferably between about 120 nm and 140 nm. In the $5^{th}$ step the LUV preparation is then subjected to a TET A treatment and dialysis to obtain the functionalized paramagnetic liposomes.

FIGS. 1 to 9 and examples thus establish the applicability and enable, inter alia, each and all which follows:

A novel method for detecting a target biochemical molecular species or at least one property correlated with the occurrence of said biochemical molecular species in a sample whose main component is water, comprising steps of (a) obtaining a sample whose main component is water; (b) providing Functionalized Paramagnetic Particles (FPP) comprising a paramagnetic core and a moiety configured to interact with said target biochemical molecular species or with molecules collectively reporting on a property of said target biochemical molecular species; (c) contacting said FPP with said sample; (d) exposing said sample to an applied magnetic field; (e) measuring a change in a nuclear relaxation property of said sample, caused by said interaction between said FPP and said biochemical molecular species or said molecules collectively reporting on a property of said target biochemical molecular species; in the applied magnetic field; and, correlating said change to the presence of said biochemical molecular species in said sample or to at least one property correlated with the occurrence of said biochemical molecular species in said sample; wherein a change in $T_1$ nuclear relaxation property of the water protons in said sample is correlated to the presence of said target biochemical molecular species or to at least one property correlated with the occurrence of said biochemical molecular species in said sample, further wherein said FPP comprises a non ferrous oxide paramagnetic core.

A method as defined in any of the above, comprising at least one additional step; said step is selected from a group consisting of one or more of the following:

a. performing two or more measurements to determine the relaxation time of the sample, wherein the measurements are performed before and after at least one addition of said FPP;

b. detecting said target biochemical molecular species and/or characterizing at least one property correlated with the occurrence of said biochemical molecular species in vitro;

c. forming said FPP as a single molecule, a multimeric system, a micro-sized vesicle or particle, a nano-sized vesicle or particle, a liposome, a probe or any combination thereof;

d. selecting said sample from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof;

e. selecting said sample from a group comprising a biological fluid, a biological tissue, a tissue extract, an industrial fluid, food sample, a beverage, wine, water, potable water, sewage, irrigation water, sea water, river water, lake water, industrial effluent, farm effluent, effluent from human habitation, road runoff, cleaning fluid, a gas sample or any combination thereof;

f. selecting said biological fluid from a group comprising urine, blood, lymph, plasma, cerebrospinal fluid, saliva, amniotic fluid, bile and tears;

g. providing said sample within a production process;

h. selecting said production process in an industrial area, said industrial area is a member of a group consisting of the pharmaceuticals, food production, beverage production, chemical refining, chemical processing, medical products, biological products, metal casting, metal refining, desalination, fluid purification, and sewage processing;

i. analyzing at least one characteristic or property of said target molecular species, said characteristic or property is selected from a group comprising concentration, permeability, oxidation state, redox characteristic (reduction-oxidation state), activation state and any combination thereof;

j. applying a magnetic field, thereby enhancing the change in a paramagnetic nuclear relaxation property of said sample upon comparing relaxation rates at two different magnetic fields;
k. measuring a change in a nuclear relaxation property of said sample using a portable NMR or MRI measuring means;
l. measuring a change in a nuclear relaxation property of said sample using a magnetic resonance device (MRD) consisting of magnets housed within a cage; and
m. measuring a change in a nuclear relaxation property of said sample using a self-fastening cage type of a magnetic resonance device (MRD).

In a self-fastening cage of a magnetic resonance device (MRD) (300), a method according to claim 1 comprising at least one additional step; said step is selected from a group consisting of one or more of the following:
a. providing a homogeneous, stable and uniform magnetic field therein, further wherein said self-fastening cage type MRD additionally characterized by an outside shell comprising at least three flexi-jointed superimposed walls (1);
b. providing an MRD characterized by an outside shell; said outside shell comprising at least three flexi-jointed superimposed walls (1) disposed in a predetermined clockwise or counterclockwise arrangement; said MRD comprising: at least six side-magnets (2) arranged in two equal groups being in a face-to-face orientation in a magnetic connection with said outside shell, increasing the overall strength of the magnetic field provided in said cage; at least two pole-magnet pieces (3), arranged in a face-to-face orientation in between said side-magnets (2); at least two main-magnets (4), located on said pole-pieces (3), arranged in a face-to-face orientation, generating the static magnetic field therein said cage; and, shimming mechanism, said mechanism is selected from a group consisting of an array of active shim coils, passive shimming elements or a combination thereof; wherein at least a portion of said side-magnets (2) are superconductors or ferromagnets;
c. providing a magnetic resonance device adapted to producing high contrast high resolution images of said sample;
d. providing a magnetic resonance device comprising: an envelope for least partially confining said sample; a plurality of magnets located at least partially around said envelope, said plurality of magnets comprising: a least one first magnet configured to provide a high magnetic field for generating multiple time-resolved one or more first images at high resolution of at least a portion of said sample; and a least one second magnet configured to provide a low magnetic field for generating multiple time-resolved one or more second images at high contrast of at least portion of same said sample; wherein at least one image of said first images and at least one image of said second images being generated in a time no greater than approximately the time between two first images; and, a CPU to process said images comprising a computer readable medium containing instructions for generating at least one third image superimposing at least one image of said first images with at least one image of said second images;
e. generating multiple time resolved one or more first images at high resolution of at least a portion of said sample; generating multiple time resolved one or more second images at high contrast of at least portion of same said sample; and then superimposing at least one image of said first images with at least one image of said second images; whereby a high-contrast, high resolution real-time continuous image of said sample is obtained;
f. selecting said at least one first magnet to be of 2 Tesla and lower;
a. selecting said at least one first magnet to be of 2 Tesla and higher;
b. said at least one first magnet from a group consisting of permanent magnets, electromagnets, superconducting magnets, and any combination thereof;
c. selecting said at least one second magnet to be of 2 Tesla and lower;
d. selecting said at least one second magnet to be of 2 Tesla and higher;
e. selecting said at least one second magnet from a group consisting of permanent magnets, electromagnets, superconducting magnets, and any combination thereof;
f. generating a magnetic resonance signal in the range of about 0.1 Tesla and about 10 Tesla;
g. generating a magnetic resonance signal in the range of 2 Tesla and lower;
h. generating a magnetic resonance signal in the range of 2 Tesla and higher;
i. applying a magnetic resonance frequency in the range of about 5 MHz to about 40 MHz;
j. selecting said magnets from a group consisting of permanent magnets, electromagnets, superconducting magnets, and any combination thereof;
k. selecting said moiety from a group comprising antibodies, antibody fragments, monoclonal antibody, receptors, ligands, macromolecules, peptides, hormones, fatty acids, lipids, receptor agonists and antagonists, amino acids, sugars, lectins, albumins, polycarbon molecules, glycoproteins, nucleic acids, pegylated molecules, liposomes, chelators, cells, viruses, chemotherapeutic agents and any combination thereof;
l. selecting said target biochemical molecular species from a group comprising a biological molecule, a chemical molecule, an analyte, a contaminant, a particle, a pathogen or any combination thereof;
m. selecting said target biochemical molecular species from a group comprising a protein, a pathogen, a prion, a virus, a bacteria, a contaminant, a pathological isoform, a biomarker, an allergen, a neurotransmitter, an antigenic determinant, an epitope, a cell marker, cell membrane marker or epitope, a membrane marker, an enzyme, a chemical molecule, an analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue and any combination thereof;
n. selecting said analyte from a group comprising an organic analyte and an inorganic analyte;
o. selecting said inorganic analyte from a group comprising molecular oxygen, oxygen-containing radicals and combinations thereof; detecting oxygen-containing radicals "ad hoc" generated, for assessing the anti-oxidant properties of the sample;
p. selecting said paramagnetic core as a metal ion, a metal complex, oxides of a metal ion, oxides of a transition metal, mixed oxides of a transition metal and their mixtures;
q. selecting said paramagnetic core from a group comprising metal complexes, aggregates of metal complexes, polymer-bound metal complexes, stable organic radicals and any combination thereof;

r. selecting said metal ion from a group comprising an ion of nickel, iron, manganese, copper, gadolinium, europium and mixtures thereof;
s. assessing redox characteristics, comprising steps of detecting differences in Paramagnetic Relaxation Enhancement (PRE) properties induced by a change in at least one redox characteristic of said FPP, using an applied magnetic field;
t. selecting said redox characteristic from a group comprising lipid peroxidation, lipid peroxidation followed by a change in membrane permeability, redox potential of metal ions, formation and cleavage of disulfide bonds, oxidation state, antioxidant activity and any combination thereof;
u. providing said FPP as a liposome loaded with a plurality of paramagnetic payloads;
v. applying a magnetic field, thereby enhancing a change in the permeability of said liposome so as to affect a nuclear relaxation property of said sample;
w. applying a magnetic field, thereby enhancing a change in at least one of cleavage or formation of disulfide bonds of said moiety so as to affect a nuclear relaxation property of said sample;
x. applying a magnetic field, thereby affecting at least one property of said FPP selected from a group comprising concentration, lipid peroxidation, membrane permeability, redox potential, formation and cleavage of disulfide bonds, oxidation state, redox potential, activation state, binding affinity, and any combination thereof, so as to induce a change in a nuclear relaxation property of said sample;
y. conjugating said liposome with a site-specific ligand;
z. conjugating said liposome with a biotin activated molecule; and
aa. providing said FPP as a biotinylated liposome.

A method for detection of a biomarker in a sample whose main component is water, comprising steps as follows:
a. obtaining a sample whose main component is water;
b. providing liposomes loaded with a plurality of paramagnetic agents, said liposomes are conjugated with a site specific moiety configured to interact with said biomarker in said sample;
c. contacting said liposomes with said sample under conditions that allow the interaction between the site specific moiety and said biomarker;
d. exposing said sample to an applied magnetic field; and,
e. measuring a change in a nuclear relaxation property of said sample caused by said interaction between the liposomes and said biomarker in the applied magnetic field;
wherein a change in $T_1$ nuclear relaxation property is correlated to the presence of said biomarker in said sample.

A method as defined above, wherein the method further comprising one or more steps as follows:
a. providing biotinylated liposomes; said liposomes loaded with a plurality of paramagnetic agents;
b. providing biotinylayed ligands, said ligands configured to interact with said biomarker;
c. providing activated avidin molecules;
d. contacting said biotinylated liposomes, said biotinylayed ligands and said activated avidin molecules with said sample so as to enable avidin-biotin interaction, thereby forming complexes comprising said liposomes, said ligand and said biomarker; such that said complexes are specific to said biomarker; and,
e. measuring a change in a nuclear relaxation property of said sample caused by said complex formation in the applied magnetic field;
wherein a change in $T_1$ nuclear relaxation property is correlated to the presence of said biomarker in said sample.

A system for detecting a target biochemical molecular species or at least one property correlated with the occurrence of said biochemical molecular species in a sample whose main component is water, comprising a magnetic resonance device (MRD) configured to measure a change in nuclear relaxation property of said sample; and, a plurality of Functionalized Paramagnetic Particles (FPP) said FPP comprising a paramagnetic core and a moiety configured to interact with said target biochemical molecular species or with molecules collectively reporting on a property of said target biochemical molecular species; wherein a change in $T_1$ nuclear relaxation property of water protons in said sample measured by said MRD is correlated to the presence of said target biochemical molecular species and/or to the at least one property correlated with the occurrence of said biochemical molecular species in said sample, further wherein said FPP comprises a non-ferrous oxide paramagnetic core.

The system as defined above wherein the system further comprising means for detecting said target biochemical molecular species and/or characterizing at least one property correlated with the occurrence of said biochemical molecular species in vitro.

The system as defined in any of the above, wherein the FPP is formed as a single molecule, a multimeric system, a micro-sized vesicle or particle, a nano-sized vesicle or particle, a liposome, a probe and any combination thereof.

The system as defined in any of the above, wherein the sample is selected from a group consisting of a liquid, a gas, a slurry, a liquid containing particulates, a gas containing particulates, a gel, a sol, a suspension, a solution, a dispersion, a colloid, a mixture, an emulsion, an aerosol, a liquid containing solid objects, a gas containing solid objects, and any combination thereof.

The system as defined in any of the above, wherein the sample is further selected from a group comprising a biological fluid, a biological tissue, a tissue extract, an industrial fluid, food sample, a beverage, wine, water, potable water, sewage, irrigation water, sea water, river water, lake water, industrial effluent, farm effluent, effluent from human habitation, road runoff, cleaning fluid, a gas sample or any combination thereof.

The system as defined in any of the above, wherein the biological fluid is selected from a group comprising urine, blood, lymph, plasma, cerebrospinal fluid, saliva, amniotic fluid, bile and tears.

The system as defined in any of the above, wherein the sample is provided within a production process.

The system as defined in any of the above, wherein the production process is in an industrial area, said industrial area is a member of a group consisting of the pharmaceuticals, food production, beverage production, chemical refining, chemical processing, medical products, biological products, metal casting, metal refining, desalination, fluid purification, and sewage processing.

The system as defined in any of the above, wherein the property is selected from a group comprising concentration, permeability, oxidation state, redox characteristic (reduction-oxidation state), activation state and any combination thereof.

The system as defined in any of the above, wherein the magnetic resonance device (MRD) is configured to enhance the change in a paramagnetic nuclear relaxation property of said sample upon comparing relaxation rates at two different magnetic fields.

The system as defined in any of the above, wherein the magnetic resonance device (MRD) is a portable NMR or MRI measuring means.

The magnetic resonance device (MRD) consists of magnets housed within a cage.

The system as defined in any of the above, wherein the magnetic resonance device (MRD) is a self-fastening cage type of a magnetic resonance device (300).

In a self-fastening cage of a magnetic resonance device (MRD) (300), a system as defined above, wherein said self-fastening cage type MRD additionally characterized by an outside shell comprising at least three flexi-jointed superimposed walls (1).

In a self-fastening cage type MRD (300), a system as defined above, said system further comprises an MRD characterized by an outside shell; said outside shell comprising at least three flexi-jointed superimposed walls (1) disposed in a predetermined clockwise or counterclockwise arrangement; said MRD comprising: at least six side-magnets (2) arranged in two equal groups being in a face-to-face orientation in a magnetic connection with said outside shell, increasing the overall strength of the magnetic field provided in said cage; at least two pole-magnet pieces (3), arranged in a face-to-face orientation in between said side-magnets (2); at least two main-magnets (4), located on said pole-pieces (3), arranged in a face-to-face orientation, generating the static magnetic field therein said cage; and, a shimming mechanism, said mechanism is selected from a group consisting of an array of active shim coils, passive shimming elements or a combination thereof; wherein at least a portion of said side-magnets (2) are superconductors or ferromagnets.

The system as defined in any of the above, wherein the MRD is configured to produce high contrast high resolution images of said sample.

The system as defined in any of the above, wherein the magnetic resonance device comprising an envelope for least partially confining said sample; a plurality of magnets located at least partially around said envelope, said plurality of magnets comprising: a least one first magnet configured to provide a high magnetic field for generating multiple time-resolved one or more first images at high resolution of at least a portion of said sample; and a least one second magnet configured to provide a low magnetic field for generating multiple time-resolved one or more second images at high contrast of at least portion of same said sample; wherein at least one image of said first images and at least one image of said second images being generated in a time no greater than approximately the time between two first images; and, a CPU to process said images comprising a computer readable medium containing instructions for generating at least one third image superimposing at least one image of said first images with at least one image of said second images, whereby a high contrast, high resolution real time continues image of said sample is obtained.

The system as defined in any of the above wherein at least one of the following is held true: said at least one first magnet is of 2 Tesla and lower; said at least one first magnet is of 2 Tesla and higher; said at least one first magnet is selected from a group consisting of permanent magnets, electromagnets, superconducting magnets, and any combination thereof; said at least one second magnet is of 2 Tesla and lower; said at least one second magnet is of 2 Tesla and higher; at least one second magnet is selected from a group consisting of permanent magnets, electromagnets, superconducting magnets, and any combination thereof; said magnetic resonance device (MRD) is configured to generate a magnetic resonance signal in the range of about 0.1 Tesla and about 10 Tesla; said magnetic resonance device (MRD) is configured to generate a magnetic resonance signal in the range of 2 Tesla and lower; said magnetic resonance device (MRD) is configured to generate a magnetic resonance signal in the range of 2 Tesla and higher; said magnetic resonance device (MRD) is configured to generate a magnetic resonance frequency in the range of about 5 MHz to about 40 MHz; said magnets are selected from a group consisting of permanent magnets, electromagnets, superconducting magnets, and any combination thereof; said moiety is selected from a group comprising antibodies, antibody fragments, monoclonal antibody, receptors, ligands, macromolecules, peptides, hormones, fatty acids, lipids, receptor agonists and antagonists, amino acids, sugars, lectins, albumins, polycarbon molecules, glycoproteins, nucleic acids, pegylated molecules, liposomes, chelators, cells, viruses, chemotherapeutic agents and any combination thereof; said target biochemical molecular species is selected from a group comprising a biological molecule, a chemical molecule, an analyte, a contaminant, a particle, a pathogen or any combination thereof; said target biochemical molecular species is selected from a group comprising a protein, a pathogen, a prion, a virus, a bacteria, a contaminant, a pathological isoform, a biomarker, an allergen, a neurotransmitter, an antigenic determinant, an epitope, a cell marker, cell membrane marker or epitope, a membrane marker, an enzyme, a chemical molecule, an analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue and any combination thereof said analyte is selected from a group comprising an organic analyte and an inorganic analyte; said inorganic analyte is selected from a group comprising molecular oxygen, oxygen-containing radicals and combinations thereof; said oxygen-containing radicals are "ad hoc" generated radicals, for assessing the anti-oxidant properties of the sample; said paramagnetic core is selected from a group comprising a metal ion, a metal complex, oxides of a metal ion, oxides of a transition metal, mixed oxides of a transition metal and their mixtures; said metal ion is selected from a group comprising an ion of nickel, iron, manganese, copper, gadolinium, europium and mixtures thereof; said redox characteristic is selected from a group comprising lipid peroxidation, lipid peroxidation followed by a change in membrane permeability, redox potential of metal ions, formation and cleavage of disulfide bonds, oxidation state, antioxidant activity and any combination thereof; said FPP is a liposome loaded with a plurality of paramagnetic payloads; said system further comprising means for enhancing a change in the permeability of said liposome so as to affect a nuclear relaxation property of said sample; said system is adapted to detect a change in at least one of cleavage or formation of disulfide bonds of said moiety so as to affect a nuclear relaxation property of said sample; said property correlated with the occurrence of said biochemical molecular species is selected from a group comprising concentration, lipid peroxidation, membrane permeability, redox potential, formation and cleavage of disulfide bonds, oxidation state, redox potential, activation state, binding affinity, and any combination thereof; said liposome is conjugated with a site-specific ligand; said liposome is conjugated with a biotin activated molecule; and said FPP is a biotinylated liposome.

A system for detection of a biomarker in a sample whose main component is water, comprising: a sample whose main component is water; liposomes loaded with a plurality of paramagnetic agents, said liposomes are conjugated with a site specific moiety configured to interact with said biomarker in said sample; a magnetic resonance device (MRD) configured to measure a change in a nuclear relaxation property of a sample whose main component is water removed from said production batch or continuous flow of said FBW or biological fluid; wherein a change in $T_1$ nuclear relaxation property of the water protons in said sample is correlated to the presence of said biomarker in said sample.

Use of Functionalized Paramagnetic Particles (FPP) to detect the presence or at least one other characteristic of a target biochemical molecular species within a sample whose main component is water, said FPP comprising a paramagnetic core and a moiety configured to interact with said target biochemical molecular species or with molecules collectively reporting on a property of said target biochemical molecular species; wherein a change in $T_1$ nuclear relaxation property of water protons within said sample measured by a generated applied magnetic field is correlated to the presence or at least one other characteristic of said target biochemical molecular species in said sample.

The use as defined above further adapted to detect at least one property correlated with the occurrence of said biochemical molecular species in said sample.

A method of establishing the redox properties of a production batch or continuous flow of a Foodstuff, Beverage or Wine (FBW) or of a biological fluid, comprising the steps of obtaining a sample removed from said production batch or continuous flow of said FBW or from said biological fluid; providing Functionalized Paramagnetic Particles (FPP) configured to change their redox property upon interaction with dissolved molecular oxygen or "ad hoc" generated radicals of said removed sample; contacting said FPP with said removed sample; exposing said removed sample to an applied magnetic field; and, measuring a change in a nuclear relaxation property of said removed sample caused by said change in the redox properties of said FPP in the applied magnetic field; wherein a change in $T_1$ nuclear relaxation property is correlated with the presence and/or concentration of said molecular oxygen or of the "ad hoc" generated radicals of said removed sample, thereby establishing the redox properties of said production batch or continuous flow of said FBW or of said biological fluid.

The method as defined above, wherein the method further comprising at least one step, said step or steps is/are selected from a group consisting of the following: providing said FPP conjugated with at least one moiety configured to interact with dissolved molecular oxygen or with "ad hoc" generated radicals; selecting said moiety from a group comprising a lipid, a fatty acid, an amino acid, a peptide, a protein, a molecule containing at least one disulfide bond, a liposome and any combination thereof; measuring a change in a nuclear relaxation property of said sample caused by a change in the antioxidant activity of said removed sample in the applied magnetic field; measuring a difference in Paramagnetic Relaxation Enhancement (PRE) property of said removed sample caused by said interaction of said FPP with said dissolved molecular oxygen or with said "ad hoc" generated radicals; contacting said removed sample with FPP configured to form a liposome structure, said FPP comprising a paramagnetic core and a fatty acid moiety, wherein peroxidation of said fatty acid moiety substantially changes the permeability of said liposome; measuring a change in a nuclear relaxation property of said removed sample based on competition for molecular oxygen consumption; providing said FPP comprising a paramagnetic core selected from a group comprising a metal ion, a metal complex, oxides of a metal ion, oxides of a transition metal, mixed oxides of a transition metal and their mixtures; selecting said metal ion from a group comprising an ion of nickel, iron, manganese, copper, gadolinium, dysprosium, europium and mixtures thereof; and selecting said biological fluid from a group comprising urine, blood, lymph, plasma, cerebrospinal fluid, saliva, amniotic fluid, bile and tears.

A system for establishing the redox properties of a production batch or continuous flow of a Foodstuff, Beverage, Wine (FBW) or of a biological fluid, comprising: a magnetic resonance device (MRD) configured to measure a change in a nuclear relaxation property of a sample removed from said production batch or continuous flow of said FBW or of said biological fluid; and, a plurality of Functionalized Paramagnetic Particles (FPP) configured to be in contact with said removed sample, said plurality of FPP are further configured to change at least one of their redox properties upon interaction with dissolved molecular oxygen or with "ad hoc" generated radicals of said removed sample; wherein a change in $T_1$ nuclear relaxation property measured by said MRD is correlated to the presence or concentration of dissolved molecular oxygen or "ad hoc" generated radicals of said removed sample, thereby the redox properties of said production batch or continuous flow of said FBW or of said biological fluid are established.

The system according as defined above, wherein said biological fluid is selected from a group comprising urine, blood, lymph, plasma, cerebrospinal fluid, saliva, amniotic fluid, bile and tears.

A system for establishing the potability of a production batch or continuous flow of a flowable Foodstuff, Beverage or Wine (FBW), comprising: a magnetic resonance device (MRD) configured to measure a change in nuclear relaxation property of a sample removed from said production batch or continuous flow of said flowable FBW; and, a plurality of functionalized paramagnetic particles (FPP) configured to be in contact with said sample, said plurality of FPP are further configured to change their redox/oxidative properties upon interaction with dissolved molecular oxygen or "ad hoc" generated radicals of said removed sample; wherein a change in $T_1$ nuclear relaxation property measured by said MRD correlates with dissolved molecular oxygen or "ad hoc" generated radicals concentration of said FBW sample, thereby establishing the potability of said production batch or continuous flow of said flowable FBW.

The system according as defined above, wherein at least one of the following is held true: a concentration value lower than about 6 ml of dissolved oxygen per liter of said removed sample is indicative of the potability of said production batch or continuous flow of said FBW; a value lower than X ml of oxygen per liter is correlated to >7 of the 9 point hedonic scale; a value lower than X ml of oxygen per liter is correlated to >y of the hybrid scale; and a value lower than X ml of oxygen per liter is correlated to >y of the self-adjusting scale.

The invention claimed is:

1. A system for detecting a target biochemical molecular species in a sample whose main component is water, comprising;
   a. a magnetic resonance device (MRD) configured to measure a change in nuclear relaxation property of said sample; and, b. a plurality of Functionalized Paramagnetic Particles (FPP) said FPP comprising a paramagnetic core and a moiety configured to interact with said target biochemical molecular species;

wherein a change in $T_1$ nuclear relaxation property of water protons in said sample measured by said MRD is correlated to the presence of said target biochemical molecular species and further wherein said FPP comprises a non ferrous oxide paramagnetic core.

2. The system according to claim 1, further comprising means for detecting said target biochemical molecular species and characterizing at least one property correlated with the occurrence of said biochemical molecular species in vitro.

3. The system according to claim 1, wherein said FPP is formed as a single molecule, a multimeric system, a micro-sized vesicle or particle, a nano-sized vesicle or particle, a liposome, a probe or any combination thereof.

4. The system according to claim 1, wherein said sample is selected from the group consisting of: a biological fluid, a biological tissue, a tissue extract, an industrial fluid, food sample, a beverage, wine, water, potable water, sewage, irrigation water, sea water, river water, lake water, industrial effluent, farm effluent, effluent from human habitation, road runoff, cleaning fluid, a gas sample and any combination thereof.

5. The system according to claim 4, wherein said biological fluid is selected from the group consisting of: urine, blood, lymph, plasma, cerebrospinal fluid, saliva, amniotic fluid, bile and tears.

6. The system according to claim 1, wherein said sample is provided within a production process.

7. The system according to claim 6, wherein said production process is in an industrial area, said industrial area is a member of a group consisting of the pharmaceuticals, food production, beverage production, chemical refining, chemical processing, medical products, biological products, metal casting, metal refining, desalination, fluid purification, and sewage processing.

8. The system according to claim 2, wherein said property is selected from the group consisting of: concentration, permeability, oxidation state, redox characteristic (reduction-oxidation state), activation state and any combination thereof.

9. The system according to claim 1, wherein said magnetic resonance device (MRD) is configured to enhance the change in a paramagnetic nuclear relaxation property of said sample upon comparing relaxation rates at two different magnetic fields.

10. The system according to claim 1, wherein said magnetic resonance device (MRD) is a portable NMR or MRI measuring means.

11. The system according to claim 1, wherein said magnetic resonance device (MRD) comprises magnets housed within a cage.

12. The system according to claim 1 wherein said magnetic resonance device (MRD) is a self-fastening cage type of a magnetic resonance device.

13. A system according to claim 1, wherein said magnetic resonance device (MRD) is a self-fastening cage magnetic resonance device, and wherein said self-fastening cage MRD additionally comprises an outside shell comprising at least three flexi-jointed superimposed walls.

14. A system according to claim 1, wherein said magnetic resonance device (MRD) is characterized by an outside shell; said outside shell comprising at least three flexi-jointed superimposed walls disposed in a predetermined clockwise or counterclockwise arrangement; said MRD comprising:
  a. at least six side-magnets arranged in two equal groups being in a face-to-face orientation in a magnetic connection with said outside shell, increasing the overall strength of the magnetic field provided in said cage;
  b. at least two pole-magnet pieces, arranged in a face-to-face orientation in between said side-magnets;
  c. at least two main-magnets, located on said pole-pieces, arranged in a face-to-face orientation, generating the static magnetic field therein said cage; and,
  d. a shimming mechanism, said mechanism is selected from the group consisting of an array of active shim coils, passive shimming elements and a combination thereof;

wherein at least a portion of said side-magnets are superconductors or ferromagnets.

15. The system according to claim 14, wherein said MRD is configured to produce high contrast high resolution images of said sample.

16. The system according to claim 14, wherein said magnetic resonance device comprises:
  a. an envelope for at least partially confining said sample;
  b. a plurality of magnets located at least partially around said envelope, said plurality of magnets comprising:
    i. at least one first magnet configured to provide a high magnetic field for generating multiple time-resolved first images at high resolution of at least a portion of said sample; and
    ii. at least one second magnet configured to provide a low magnetic field for generating multiple time-resolved second images at high contrast of at least a portion of said sample; and
  c. a CPU to process said images comprising a computer readable medium containing instructions for generating at least one third image superimposing at least one image of said first images with at least one image of said second images, whereby a high contrast, high resolution, real time continuous image of said sample is obtained.

17. The system according to claim 16, wherein at least one of the following is held true:
  a. said at least one first magnet is of 2 Tesla and lower;
  b. said at least one first magnet is of 2 Tesla and higher;
  c. said at least one first magnet is selected from the group consisting of permanent magnets, electromagnets, superconducting magnets, and any combination thereof;
  d. said at least one second magnet is of 2 Tesla and lower;
  e. said at least one second magnet is of 2 Tesla and higher;
  f. said at least one second magnet is selected from the group consisting of permanent magnets, electromagnets, superconducting magnets, and any combination thereof;
  g. said magnetic resonance device (MRD) is configured to generate a magnetic resonance signal in the range of about 0.1 Tesla and about 10 Tesla;
  h. said magnetic resonance device (MRD) is configured to generate a magnetic resonance signal in the range of 2 Tesla and lower;
  i. said magnetic resonance device (MRD) is configured to generate a magnetic resonance signal in the range of 2 Tesla and higher;
  j. said magnetic resonance device (MRD) is configured to generate a magnetic resonance frequency in the range of about 5 MHz to about 40 MHz;

k. said magnets are selected from the group consisting of permanent magnets, electromagnets, superconducting magnets, and any combination thereof;
l. said moiety is selected from the group consisting of antibodies, antibody fragments, monoclonal antibody, receptors, ligands, macromolecules, peptides, hormones, fatty acids, lipids, receptor agonists and antagonists, amino acids, sugars, lectins, albumins, polycarbon molecules, glycoproteins, nucleic acids, pegylated molecules, liposomes, chelators, cells, viruses, chemotherapeutic agents and any combination thereof;
m. said target biochemical molecular species is selected from the group consisting of a biological molecule, a chemical molecule, an analyte, a contaminant, a particle, a pathogen and any combination thereof;
n. said target biochemical molecular species is selected from the group consisting of a protein, a pathogen, a prion, a virus, a bacteria, a contaminant, a pathological isoform, a biomarker, an allergen, a neurotransmitter, an antigenic determinant, an epitope, a cell marker, cell membrane marker or epitope, a membrane marker, an enzyme, a chemical molecule, an organic analyte, an inorganic analyte, a receptor, a ligand, a macromolecule, a peptide, a hormone, a fatty acid, a lipid, a receptor agonist and antagonist, an amino acid, a sugar, a glycoprotein, a nucleic acid, an antioxidant agent, a chemotherapeutic agent, a biological tissue and any combination thereof;
o. said target biochemical molecular species is an inorganic analyte selected from the group consisting of: molecular oxygen, oxygen-containing radicals and combinations thereof;
p. said target biochemical molecular species is an inorganic analyte, wherein said inorganic analyte is an oxygen-containing radical and said oxygen-containing radicals are "ad hoc" generated radicals, for assessing the anti-oxidant properties of the sample;
q. said paramagnetic core is selected from the group consisting of a metal ion, a metal complex, oxides of a metal ion, oxides of a transition metal, mixed oxides of a transition metal and their mixtures;
r. said paramagnetic core is selected from the group consisting of a metal ion, a metal complex, oxides of a metal ion, oxides of a transition metal, mixed oxides of a transition metal and their mixtures and wherein said metal ion is selected from the group consisting of an ion of nickel, iron, manganese, copper, gadolinium, europium and mixtures thereof;
s. said FPP is a liposome loaded with a plurality of paramagnetic payloads;
t. said FPP is a liposome wherein said system further comprises means for enhancing a change in the permeability of said liposome so as to affect a nuclear relaxation property of said sample;
u. said system is adapted to detect a change in at least one of cleavage or formation of disulfide bonds of said moiety so as to affect a nuclear relaxation property of said sample;
v. said FPP is a liposome and said liposome is conjugated with a site-specific ligand;
w. said FPP is a liposome and said liposome is conjugated with a biotin activated molecule; and
x. said FPP is a biotinylated liposome.

* * * * *